(12) United States Patent  
Cao

(10) Patent No.: US 7,855,068 B2
(45) Date of Patent: Dec. 21, 2010

(54) METHODS AND KITS FOR DETECTING A TARGET CELL

(75) Inventor: Bo Cao, Shanghai (CN)

(73) Assignee: Semibio Holdings Limited, George Town (KY)

( * ) Notice: Subject to any disclaimer, the term of this patent is extended or adjusted under 35 U.S.C. 154(b) by 1894 days.

(21) Appl. No.: 10/420,643

(22) Filed: Apr. 22, 2003

(65) Prior Publication Data

US 2004/0009471 A1 Jan. 15, 2004

Related U.S. Application Data

(63) Continuation-in-part of application No. 10/132,543, filed on Apr. 25, 2002.

(51) Int. Cl.
| | |
|---|---|
| *C12M 1/34* | (2006.01) |
| *C12Q 1/00* | (2006.01) |
| *C12Q 1/68* | (2006.01) |
| *G01N 33/53* | (2006.01) |

(52) U.S. Cl. ............... 435/287.2; 435/4; 435/6; 435/7.1; 435/7.9; 435/283.1; 435/518; 422/61

(58) Field of Classification Search ............ None
See application file for complete search history.

(56) References Cited

U.S. PATENT DOCUMENTS

| | | | |
|---|---|---|---|
| 4,357,142 A | | 11/1982 | Schall, Jr. et al. |
| 4,581,223 A | * | 4/1986 | Kass ............... 435/34 |
| 4,591,570 A | | 5/1986 | Chang |
| 4,677,061 A | | 6/1987 | Rose et al. |
| 4,717,545 A | * | 1/1988 | Morris ............ 422/56 |
| 4,933,278 A | * | 6/1990 | Connolly ......... 435/29 |
| 4,952,519 A | | 8/1990 | Lau |
| 5,066,582 A | | 11/1991 | Tsuruta et al. |
| 5,100,777 A | | 3/1992 | Chang |
| 5,208,111 A | | 5/1993 | Decher et al. |
| 5,246,832 A | * | 9/1993 | Michelson et al. ...... 435/7.2 |
| 5,296,381 A | * | 3/1994 | Yafuso et al. ............ 436/172 |
| 5,340,719 A | | 8/1994 | Hajek et al. |
| 5,348,859 A | | 9/1994 | Brunhouse et al. |
| 5,554,505 A | | 9/1996 | Hajek et al. |
| 5,556,760 A | | 9/1996 | Nakamura et al. |
| 5,602,042 A | * | 2/1997 | Farber ............ 436/526 |
| 5,643,721 A | | 7/1997 | Spring et al. |
| 5,658,732 A | | 8/1997 | Ebersole et al. |

(Continued)

FOREIGN PATENT DOCUMENTS

| | | |
|---|---|---|
| EP | 0 223 978 | 8/1992 |
| EP | 762122 A1 * | 3/1997 |
| WO | WO 88/07201 | 9/1988 |
| WO | WO 01/11362 | 2/2001 |
| WO | WO 03/091394 A2 | 11/2003 |
| WO | WO 03/091394 A3 | 11/2003 |

OTHER PUBLICATIONS

JP Patent Abstract No. 04056250 published on Aug. 24, 1993.

(Continued)

*Primary Examiner*—Robert T. Crow
(74) *Attorney, Agent, or Firm*—Perkins Coie LLP

(57) ABSTRACT

The present invention concerns the identification of specific target cells in whole blood. The present invention discloses methods for detecting and optionally quantifying a target cell in untreated or substantially untreated whole blood. The present invention further discloses kits for detecting and optionally quantifying a target cell in untreated or substantially untreated whole blood.

44 Claims, 2 Drawing Sheets

A

B

C

U.S. PATENT DOCUMENTS

| | | | |
|---|---|---|---|
| 5,658,745 | A | 8/1997 | Greene et al. |
| 5,674,696 | A | 10/1997 | Nakamura et al. |
| 5,711,915 | A * | 1/1998 | Siegmund et al. .......... 422/68.1 |
| 5,716,854 | A | 2/1998 | Lofas et al. |
| 5,866,350 | A | 2/1999 | Canavaggio et al. |
| 5,879,951 | A * | 3/1999 | Sy .............................. 436/514 |
| 5,880,835 | A * | 3/1999 | Yamazaki et al. ........... 356/336 |
| 6,017,496 | A | 1/2000 | Nova et al. |
| 6,025,126 | A * | 2/2000 | Westbrook ...................... 435/6 |
| 6,063,637 | A | 5/2000 | Arnold et al. |
| 6,132,961 | A * | 10/2000 | Gray et al. ...................... 435/6 |
| 6,207,369 | B1 * | 3/2001 | Wohlstadter et al. ........... 435/6 |
| 6,303,325 | B1 * | 10/2001 | Mehta et al. ................. 435/7.5 |
| 6,379,910 | B1 | 4/2002 | Nakamura et al. |
| 6,461,825 | B1 | 10/2002 | Carriere |
| 6,689,478 | B2 | 2/2004 | Laguitton |
| 6,716,588 | B2 | 4/2004 | Sammak et al. |
| 6,766,817 | B2 | 7/2004 | da Silva |
| 6,767,733 | B1 | 7/2004 | Green |
| 7,141,369 | B2 | 11/2006 | Cao |
| 2001/0041347 | A1 | 11/2001 | Sammak et al. |
| 2001/0049108 | A1 * | 12/2001 | McGall et al. ................. 435/6 |
| 2002/0076833 | A1 | 6/2002 | Henry et al. |
| 2002/0192676 | A1 | 12/2002 | Madonna et al. |

OTHER PUBLICATIONS

JP Patent Abstract No. 06243778 published on Apr. 30, 1996.
Kam et al., Clin. Diagn. Lab. Immunol: 3(3):326-330, 1996.
Pascale et al., Clin. Diagn. Lab. Immunol: 4(4):474-477, 1997.
Kannangai et al., Clin. Diagn. Lab. lmmunol: 8(6):1286-1288, 2001.
Documents from http://www.affordcd4.com, 2004.
Abstract: Greenberg et al., Blood 65(1):190, 1985.
Abstract: Randall, J Immunol Methods, 60(1-2) 147, 1983.
Abstract: Morhenn et al., JID 81:127s, 1983.
Abstract: Wood et al., JID 84(1):37, 1985.
Abstract: Bundesen et al., J Immunol Methods 30(2):179, 1979.
Abstract: Nash, J Immunol Methods 12(1-2):149, 1976.
Abstract: Vakkila et al., Immunol Lett (15(3):229, 1977.
Abstract: Bash et al., J Immunol Methods 56(3):269, 1983.
Abstract: Tsoi et al., J Immuno Methods 53(3):293, 1982.
Abstract: Ralph et al., Stem Cells 2(2):88, 1984.
Abstract: Smedman et al., Am J Trop Med Hyg 41(1):116, 1989.
Abstract: Burgess et al., J Immunol Methods 227(1-2):169, 1999.
Abstract: Morecki et al., J Biol Response Mod 9(5):463, 1990.
Abstract: Larsson et al., J Immunol Methods 116(2):293, 1989.
Abstract: Gee et al., J Immunol Methods 142(1):127, 1991.
Abstract: Nordon et al., Cytometry 16(1):25, 1994.

* cited by examiner

A

B

C

METHODS AND KITS FOR DETECTING A TARGET CELL

The present application is a continuation-in-part of the following application, which is incorporated by reference in its entirety herein: U.S. patent application Ser. No. 10/132,543 to Cao, entitled "Measurement of the cell activity and cell quantity", filed on Apr. 25, 2002.

TECHNICAL FIELD

The present invention relates generally to the field of diagnostics, and more specifically concerns methods and kits for detecting a target cell in a sample of untreated or substantially untreated whole blood.

BACKGROUND

The different cells found in blood may be immunologically distinguished from one another by antigens found on the cell surface. For example, subsets of lymphocytes, the cells of the immune system that specifically recognize and respond to foreign antigens, can be distinguished by "Cluster of Differentiation" antigens or CD antigens, which are cell-surface antigens that can be recognized by specific antibodies. Helper T-lymphocytes that display the CD4 antigen are known as $CD4^+$ T-lymphocytes. $CD4^+$ T-lymphocytes are important to maintaining an immune defense, since they help to induce B-lymphocyte differentiation and production of specific antibodies and to regulate other lymphocyte responses.

The causative agent of Acquired Immune Deficiency Syndrome (AIDS) in humans, Human Immunodeficiency Virus (HIV), primarily infects $CD4^+$ T-lymphocytes. HIV infection and the progress of AIDS disease are marked by a decrease in $CD4^+$ T-lymphocytes. Absolute CD4+ T-lymphocyte counts and the change in these counts over time are clinically important markers of viral infection, disease progression, and therapy efficacy, as well as valuable prognostic indicators in HIV-infected patients. The ability to monitor CD4+ T-lymphocyte levels is important in surveillance of AIDS incidence, in studying the effects of antiviral therapy, and in making decisions about therapeutic strategies, including decisions to initiate prophylaxis for opportunistic infections such as *Pneumocystis carinii* pneumonia.

The current benchmark method for measuring absolute $CD4^+$ T-lymphocyte counts is based on immunotyping by flow cytometry, usually in combination with a hematology analyzer ("multi-platform" or "dual-platform" technology) (Anonymous, 1997, *Morbidity and Mortality Weekly Report*, 46(RR-2):1-29). The absolute $CD4^+$ T-lymphocyte count is commonly based on three measurements: a white blood cell count, the percentage of WBCs that are lymphocytes ("differential") (both obtained by a hematology analyzer), and the percentage of lymphocytes that are $CD4^+$ T-lymphocytes (obtained by flow cytometric immunotyping). More recent "single-platform" technology uses flow cytometry and internal calibration standards to give absolute $CD4^+$ T-lymphocyte counts (Mandy et al., 2003, *Morbidity and Mortality Weekly Report*, 52(RR02): 1-13). Unfortunately, flow cytometry requires expensive instrumentation and specialized technical training, which generally limits this method to those countries that have the resources to afford it. Both developed countries and underdeveloped, resource-poor countries have a great need for diagnosing and monitoring HIV infection and AIDS disease progression, but the latter often cannot afford routine flow cytometry. The incidence of HIV infection and AIDS disease is high in many such underdeveloped countries, and there is an urgent need for an inexpensive, simple, and accurate method for reliably measuring absolute $CD4^+$ T-lymphocyte counts.

BRIEF DESCRIPTION OF THE FIGURES

FIG. 1A depicts a schematic diagram of a solid substrate comprising a glass slide with an antibody-coated chamber such as described in Example 4. FIG. 1B depicts a schematic diagram of a reference slide including a grid pattern such as described in Example 4. FIG. 1C depicts a schematic diagram of a solid substrate comprising a slide with multiple antibody-coated chambers.

SUMMARY

Figure 1:
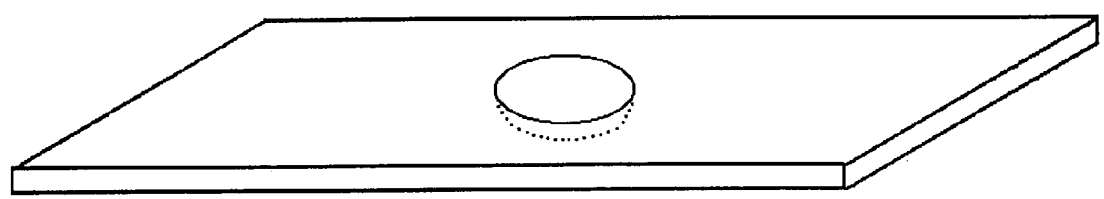
FIG. 1 depicts one embodiment of the solid substrate such as described in Example 4.
Figure 1:
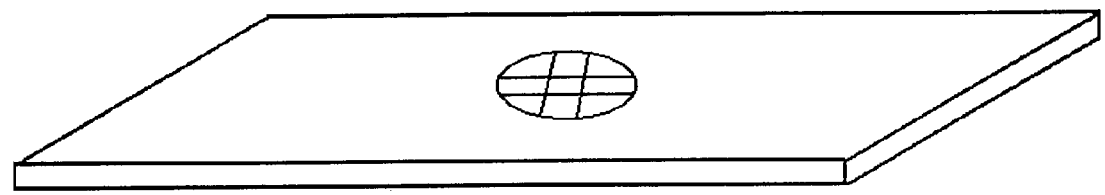
Figure 1:
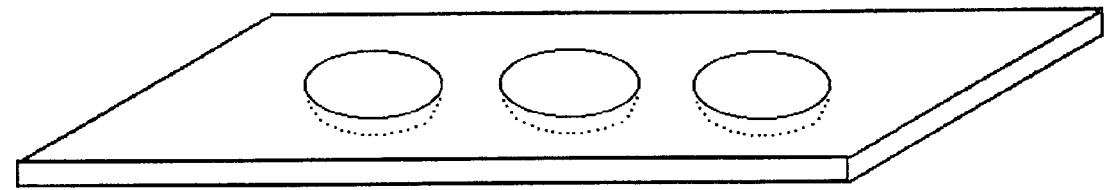

The present invention answers the urgent need for an inexpensive, technically simple, accurate method for detecting and optionally quantifying a specific target cell, such as a $CD4^+$ T-lymphocyte, in a sample, such as a sample of whole blood. The present invention provides a method for detecting a target cell in a sample of untreated or substantially untreated whole blood, which includes the steps of binding a target cell contained in the sample to a solid substrate that comprises a multi-layered composition comprising a specific binding agent that specifically binds the target cell. The present invention also provides kits for carrying out the method of the invention.

DETAILED DESCRIPTION OF THE INVENTION

Unless defined otherwise, all technical and scientific terms used herein have the same meaning as commonly understood by one of ordinary skill in the art to which this invention belongs. Generally, the nomenclature used herein and the manufacture or laboratory procedures described below are well known and commonly employed in the art. Conventional methods are used for these procedures, such as those provided in the art and various general references.

Where a term is provided in the singular, the inventors also contemplate the plural of that term. The nomenclature used herein and the laboratory procedures described below are those well known and commonly employed in the art. Where there are discrepancies in terms and definitions used in references that are incorporated by reference, the terms used in this application shall have the definitions given herein. Other technical terms used herein have their ordinary meaning in the art that they are used, as exemplified by a variety of technical dictionaries (for example, Chambers Dictionary of Science and Technology, Peter M. B. Walker (editor), Chambers Harrap Publishers, Ltd., Edinburgh, UK, 1999, 1325 pp.). The inventors do not intend to be limited to a mechanism or mode of action. Reference thereto is provided for illustrative purposes only.

I. Method for Detecting a Target Cell

The present invention provides a method for detecting a target cell in a sample of untreated or substantially untreated whole blood. The method can include the steps of: a) providing a sample of untreated or substantially untreated whole blood that is suspected of containing a target cell; b) providing a solid substrate, wherein the solid substrate comprises a multi-layered composition comprising a specific binding agent that specifically binds the target cell; c) contacting the sample with the solid substrate; d) incubating the sample on the solid substrate for a period of time sufficient to permit the specific binding agent to bind the target cells present in the sample; e) washing the solid substrate; and f) detecting the target cells bound to the solid substrate. Preferably, a target cell is detected in the sample of untreated or substantially untreated whole blood. The method can further include the step of quantifying the target cells bound to the solid substrate. The method can have an accuracy of detection and quantification of a target cell bound to the solid substrate that correlates with detection and quantification by flow cytometric detection.

The detecting of a target cell bound to the solid substrate can correlate with diagnosis of a health condition, or with prognosis of a health condition, or with monitoring of a health condition. The health condition may be any one or more of the health conditions including, but not limited to, acquired immune deficiency disorders (such as human immunodeficiency virus-caused Acquired Immune Deficiency Syndrome or AIDS), congenital immune deficiency disorders, leukemias (such as acute lymphocytic leukemia), non-leukemia cancers (such as multiple myeloma or Hodgkin's lymphoma), idiopathic lymphocytopenias (such as idiopathic $CD4^+$ T-lymphocytopenia), bacterial infections, and viral infections (such as human immunodeficiency virus infections).

Target Cell

The target cell to be detected by the method of the invention may be any target cell of interest that is found in whole blood. Suitable target cells include erythrocytes, lymphocytes (including B-lymphocytes, T-lymphocytes, and natural killer lymphocytes), monocytes, megakaryocytes, granulocytes (including neutrophils, eosinophils, and basophils), hematopoietic stem cells, hematopoietic progenitor cells, dendritic cells, Langerhans cells, epithelial cells, fibroblasts, metastatic cancer cells, and circulating fetal cells. More preferably, a target cell may be a $CD4^+$ T-lymphocyte, a $CD8^+$ T-lymphocyte, a $CD3^+$ T-lymphocyte, a $CD19^+$ B-lymphocyte, a $CD23^+$ B-lymphocyte, a $CD25^+$ T-lymphocyte, a $CD56^+$ natural killer lymphocyte, a $CD65^+$ lymphocyte, or a $CD34^+$ hematopoietic progenitor cell.

Whole Blood

The sample of whole blood is untreated or substantially untreated whole blood suspected of containing a target cell. The method of the present invention is more convenient and simpler than other cell analysis methods that require the sample to undergo substantial additional preparation steps (such as, but not limited to, erythrocyte lysis, cell concentration, centrifugation, filtration, buffy coat preparation, plasma removal, serum removal, or isolation of a group of cells) before analysis. "Substantially untreated whole blood" refers to whole blood that has not been subjected to one or more of the following treatments: erythrocyte lysis, cell concentration, centrifugation, filtration, buffy coat preparation, plasma removal, serum removal, or isolation of a group of cells (such as isolation of leukocytes from whole blood). "Substantially untreated whole blood" may be treated with an anticoagulant, such as an EDTA salt, a citrate salt (for example, ACD), or heparin. "Substantially untreated whole blood" may for convenience be diluted with a suitable diluent that does not substantially alter cell counts (including cell counts of erythrocytes or of white blood cells), such as sterile saline, for example when it is desirable to decrease sample viscosity or to facilitate handling of very small volumes of sample. The sample of substantially untreated whole blood may optionally have added to it one or more accessory reagents that do not interfere with the binding of a target cell to the solid substrate, do not substantially alter the cells (including erythrocytes and white blood cells) in the whole blood, and do not substantially alter the accuracy of a method of the invention (for example, as indicated by correlation of cell counts obtained by a method of the invention with cell counts obtained by flow cytometric methods). The sample of untreated whole blood may also be used directly, for example, used directly from a whole blood collection device (such as a needle and syringe or a lancet) or dropped directly onto the solid substrate (such as from a finger puncture), without treatment with an anticoagulant or without dilution. Preferably, the sample of whole blood may be analyzed by the method of the invention within a relatively short period of time (within about six hours) after the sample is collected. Preferably, the sample of whole blood need not be refrigerated or otherwise chilled.

Solid Substrate

The solid substrate of the invention can be substantially optically transparent, at least in the area of the substrate where bound target cells are to be detected by the method of the invention. The solid substrate can be glass, quartz, silicon, silica oxides, ceramics, polymeric plastics, cycloolefins and copolymers thereof, cellulose polymers, metals, or composites made up of a combination of these materials. Glass includes silicate glass, silica carbonate glass, soda lime silica glass, as well as non-silicon-based glasses such as polymeric glasses. Polymeric plastics include but are not limited to polystyrenes, polypropylenes, polyolefins, polycarbonates, polyacrylamides, polyacrylates, polynitriles, polyurethanes, polyesters, polyethers, polyphenylenes, silicones, fluorocarbons, and the like. Polymeric plastics may include linear, branched, and substituted polymers. Polymers may also be derived from biological substances, such as cellulose and other polysaccharides, silk and other polypeptides, and latex and other natural rubbers. Cellulose polymers include for example cellulose acetates, cellulose esters, and cellulose nitrates. All of these materials may be used singly or in combination as composites, for example, in combination as mixed polymers such as a polyamide-polyethylene copolymer, or in combination as composites such as plastic-coated glass laminates. The solid substrate may be further treated in order to modify its surface. For example, the solid substrate may be cleaned, chemically or electrostatically activated, etched, textured, smoothened, or otherwise modified in order to improve its performance in the method of the present invention.

In one embodiment of the invention, the solid substrate is preferably optically transparent. This may be advantageous, for example, when detection of the target cell is by means of a simple or compound light microscope. The solid substrate may be optically transparent in some areas and non-optically transparent in other areas, for example, a slide that is opaque in some areas and optically transparent in other areas. In other embodiments of the invention, non-optically transparent solid substrates may also be used, for example, when the target cell is detectable by optical wavelengths reflecting off the solid substrate.

In one aspect of the invention, the solid substrate comprises a substantially planar surface. The substantially planar surface need not be perfectly flat and may be flexible. Examples of substantially planar surfaces include but are not limited to glass slides, chips made out of glass (such as glass cover slips) or of other suitable materials such as quartz or plastic polymers, the bottom surface of a well (such as a well in a multi-well plate), nonporous films or membranes, porous films or membranes, filters, meshes, or grids. The solid substrate may be of any shape, including square, rectangular, round, ovoid, or irregular or of other shape, that is convenient for a particular application. The size of the solid substrate may be any size that is convenient for a particular application, preferably a size that enhances or optimizes efficient and cost-effective detection of a target cell. Factors that may be considered in the design of the solid substrate include, but are not limited, to the type and relative abundance of a target cell in the sample, the nature of the binding interaction between the specific binding agent and the target cell, the costs of the reagents and of manufacturing the solid substrate, and ease and efficiency of operation.

In another aspect of the invention, the solid substrate comprises a chamber. Such a chamber may be of predetermined dimensions, to hold a predetermined volume of sample. The volume of sample is selected to preferably give a sufficient volume for an accurate detection and optional quantification of a target cell, such as from about 1 nanoliter to about 100,000 microliters, or from about 1 microliter to about 1000 microliters, or from about 1 microliter to 20 microliters. The dimensions of the chamber may be of any dimensions necessary to hold the volume of sample, either as a single aliquot or as a flow-through sample with a volume that is larger than the chamber's volume. The dimensions of the chamber may permit it to hold from about 1 nanoliter to about 100,000 microliters, or from about 1 microliter to about 1000 microliters, or from about 1 microliter to 20 microliters. Preferably, the dimensions of the chamber are selected to enhance or optimize efficient and cost-effective detection of a target cell. The chamber may be of any shape or size suitable to assaying a particular target cell, and need not be enclosed on all sides. One embodiment includes a glass slide that has on one surface a concave depression of sufficient depth to contain a liquid within the depression. A chamber formed by such a depression may be optionally further enclosed, for example, by placing a cover slip over the chamber. A chamber formed by such a depression may be manufactured to hold a predetermined volume of sample. The chamber may be elongated, such as a chamber formed by a tubular or cylindrical structure. The chamber may have one or more dimensions that is relatively small or that is relatively large, such as in a capillary tube. The chamber may hold a predetermined volume of sample that is introduced into the chamber as a single aliquot. It is also possible to flow a volume of sample through the chamber that is larger than the chamber's volume. The chamber may be fitted with an inlet and with an outlet, such as with an inlet tube and with an outlet tube.

The solid substrate may also include a pattern of predetermined dimensions. Such a pattern may be of a grid, a checkerboard, concentric circles, or any pattern useful in detecting and optionally quantifying target cells bound to the solid substrate. For example, the pattern selected may have marks, such as lines forming a grid or checkerboard, delineating areas, preferably discrete areas of from about 0.0025 square millimeters to about 1 square millimeters, or from about 0.0025 square millimeters to about 0.1 square millimeters, or from about 0.0025 square millimeters to about 0.04 square millimeters. One embodiment of a substrate comprising a pattern of predetermined dimensions is a glass slide that has on one surface a chamber consisting of a concave depression of sufficient depth to contain a liquid within the depression, and that has a grid pattern printed, etched, or otherwise visibly marked on or projected onto the glass slide, particularly in the area of the chamber. In another embodiment, a pattern of predetermined dimensions is located on a separate reference slide, which may be used in conjunction with a second glass slide that has on one surface a chamber. When the two slides are aligned, the chamber and the grid pattern visually overlap, at least in part, thus visually dividing the chamber into discrete areas for convenience of an observer in detecting cells bound to the chamber.

Multi-Layered Composition Including a Specific Binding Agent

The multi-layered composition of the present invention comprises polyanion layers and polycation layers in an alternating arrangement that is substantially parallel to the surface of the solid substrate. The multi-layered composition may comprise one or more polyanion layer, and one or more polycation layer. Preferably, the multi-layered composition comprises at least three polyionic (polyanionic or polycationic in an alternating arrangement) layers. The multi-layered composition may comprise up to about 5 polyionic layers, or up to about 10 polyionic layers, or up to about 30 polyionic layers. Each polyanion layer may be the same or different as another polyanion layer. Each polycation layer may be the same or different as another polycation layer. The first layer adjacent to the surface of the solid substrate may be a polyanionic layer or a polycationic layer. Each polyanion layer is believed to be bound to each adjacent polycation layer primarily by electrostatic forces; however, applicants do not intend to be limited to such a proposed mechanism.

Each polyionic layer may comprise monomeric compounds bearing the same charge, or polymeric compounds bearing the same charge, or a combination of monomers and polymers all bearing the same charge. A polyanionic layer may comprise one or more monomeric compounds bearing one or more negative charges, or one or more polymeric compounds bearing multiple negative charges, or a combination of negatively charged monomers and polymers. A polycationic layer may comprise one or more monomeric compounds bearing one or more positive charges, or one or more polymeric compounds bearing multiple positive charges, or a combination of positively charged monomers and polymers. In an alternative embodiment, a polyionic layer may comprise amphiphilic monomers or amphiphilic polymers or a combination thereof. See, generally, U.S. Pat. No. 5,208,111, issued May 4, 1993, to Decher et al., which is herein incorporated in its entirety.

Suitable polyanions that may be used in the method of the invention include polyphosphorus acids (for example, polyphosphoric, polyphosphonic, and polyphosphinic acids), polysulfur acids (for example, polysulfuric acids, polysulfonic acids, polysulfinic acids, polysulfenic acids, polysulfanilic acids, polysulfamidic acids, and polysulfamic acids), polyboric acids, polysilicic acids, polycarboxylic acids, anionic polyaminoacids, anionic polypeptides, anionic polyols, anionic polythiols, anionic polyimides, and combinations thereof. Anionic monomers of the above polyanions may optionally also be used. Suitable polycations that may be used in the method of the invention include polyamines (for example, chitin, chitosan, glucosamine, poly-ornithine, and the like), polyaminiums, polyammoniums, polyphosphoniums, polyyliums, polyoxoniums, cationic polyols, cationic polythiols, cationic polyaminoacids (such as poly-lysine and poly-arginine), cationic polyaldehydes, and combinations thereof. Cationic monomers of the above polycations may optionally also be used. The polyionic (polycationic or polyanionic) layers may be derived from commercially available reagents, thus avoiding the need for chemical synthesis.

The solid substrate itself may, if suitably charged, act in effect as a foundation polyionic layer; for example, when the solid substrate is a silica glass that has been treated with a strong alkali solution (such as a strong sodium hydroxide or potassium hydroxide solution), or when the solid substrate is treated in a manner that ionizes the surface (such as by treatment with high voltage or plasma or appropriate chemical modification), or when the solid substrate has a naturally ionized surface (as occurs, for example, in mica, certain ceramics, and certain biologically derived polymers).

The multi-layered composition of the present invention further includes a specific binding agent that specifically binds the target cell of interest. The specific binding agent may be located on one or more loci on the solid support. For example, the specific binding agent may be located on or more chambers on a single glass slide, or on the bottoms of one or more wells in a multi-well plate. The specific binding agent may be an intact antibody, such as a polyclonal or a monoclonal antibody. The specific binding agent may be an antibody fragment, such as an antigen-binding fragment or Fab, or, an $F(ab')_2$ fragment, or the antigen-binding site of an antibody (such as a complementarity-determining region of an antibody). In some embodiments, the specific binding agent is preferably a purified, high affinity monoclonal antibody that specifically binds the target cell of interest. The specific binding agent may in other embodiments be an antigen, a ligand, or a receptor. The specific binding agent may bind to more than one type of cell, but preferably binds only one type of target cell that is found in a sample of whole blood. The specific binding agent may be comprised of more than one reagent; for example, the specific binding agent may comprise more than one type of monoclonal antibody or antibody fragment, each of which specifically binds the same type of target cell.

The multi-layered composition may further include a high affinity binding pair that serves to attach the specific binding agent to the solid substrate by a non-covalent binding reaction. Suitable high affinity binding pairs include avidin and biotin, any protein that binds an immunoglobulin, and a ligand-receptor pair. Avidin includes avidin, modified avidin (such as deglycosylated avidin), streptavidin, and derivatives thereof, which bind biotin or its derivatives with high affinity. Proteins that bind an immunoglobulin include protein A, protein G, and protein L, and can be selected for their immunoglobulin specificity. Examples of ligand-receptor pairs that can serve as a high affinity binding pair include a small molecule and a macromolecule that binds the small molecule (for example, folic acid and a folate binding protein), and an antigen-antibody pair or hapten-antibody pair (for example, nitrophenol and anti-nitrophenol antibody).

The high affinity binding pair may be used to attach the specific binding agent to the solid substrate by either of two techniques. In the first technique, the first member of the high affinity binding pair is affixed to the multi-layered composition, preferably to the top polyionic layer of the multi-layered composition, and preferably by a covalent bond. The second member of the high affinity binding pair is affixed to the specific binding agent, preferably in a manner that does not substantially change the ability of the specific binding agent to bind to the target cell, and preferably but not necessarily by a covalent bond. When affixing either or both members of the high affinity binding pair, the use of a linking arm may be desirable, for example to provide sufficient flexibility for the specific binding agent to bind the target cell.

In the second technique, the high affinity binding pair is characterized by multivalency. For example, avidin and its homologues are capable of binding up to four molar equivalents of biotin. In this second technique, one unit of the first member (for example, biotin) of the high affinity binding pair is affixed to the multi-layered composition, preferably to the top polyionic layer of the multi-layered composition, and preferably by a covalent bond. A second unit of the first member of the high affinity binding pair is affixed to the specific binding agent, preferably in a manner that does not substantially change the ability of the specific binding agent to bind to the target cell, and preferably but not necessarily by a covalent bond. The two units of the first member of the binding pair both bind to the second member (for example, avidin) of the high affinity binding pair, thus attaching the specific binding agent to the solid substrate by a non-covalent bond. When affixing either or both members of the high affinity binding pair, the use of a linking arm may be desirable, for example to provide sufficient flexibility for the specific binding agent to bind the target cell.

Incubating

The method of the present invention includes the steps of contacting and incubating a sample of untreated or substantially untreated whole blood that is suspected of containing a target cell with a solid substrate that comprises a multi-layered composition comprising a specific binding agent that specifically binds the target cell. By contacting is meant bringing the sample in liquid contact with the solid substrate. For example, the sample may be transferred by pipette, syringe, tubing, pump, or directly dropping onto the solid substrate.

The sample is incubated on the solid substrate in order to permit the specific binding agent to bind the target cells present in the sample. When it is desired to quantify as well as to identify a target cell, quantitative or near-quantitative binding of the target cells present in the sample is preferably achieved, preferably in a manner that facilitates detection and identification of a target cell (such as by quantitative or near-quantitative binding of the target cells in a single layer of cells on the solid substrate). This binding is dependent upon several factors, including the nature of the binding interaction between the specific binding agent and the target cell, the effective concentration of the specific binding agent or of the target cell, and the temperature, humidity, pH, ionic strength, period of time of incubation, and other incubation conditions. Certain factors may be more easily or more conveniently controlled. The effective concentration of the specific binding agent may be increased or decreased as needed, by changing the reaction conditions (for example, type or concentration of reagents) used in the manufacture of the multi-layered composition including a specific binding agent. Two factors that are simple and inexpensive to control and standardize are the period of time of incubation and the incubation temperature. The sample is incubated on the solid substrate for a period of time sufficient to permit the specific binding agent to bind the target cells present in the sample. Preferably this period of time is sufficient to permit the quantitative or near-quantitative binding of the target cells present in the sample. The period of time may be from about 5 minutes to about 300 minutes, or about 10 minutes to about 120 minutes, or about 10 minutes to about 60 minutes. For convenience, the period of time is preferably a relatively short period of time, such as 20 to 30 minutes.

The incubation temperature may also be controlled as desired for enhanced or optimal binding of the target cell to the solid substrate. Temperatures that are excessively high or excessively low may lyse or otherwise damage the sample. Incubation may be carried out at a temperature of between about 4 degrees Celsius and about 40 degrees Celsius, or between about 10 degrees Celsius and about 37 degrees Celsius, or between about 15 degrees Celsius and about 30 degrees Celsius.

Since the sample should remain fluid during incubation on the solid substrate, it may be desirable to maintain a relatively humid atmosphere around the sample while it is being incubated, particularly if there is a possibility of the sample drying out (for example, if the sample is of a very small volume). This may be conveniently achieved by incubating the sample in a humid compartment.

After the sample has been incubated on the solid substrate, the solid substrate is washed. This may be by means of rinsing or irrigating or flushing with a suitable wash solution, such as sterile saline or phosphate-buffered saline solution. Preferably, the washing step effectively removes unbound components of the sample from the solid substrate, but does not substantially remove target cells bound by the specific binding agent to the solid substrate, nor interferes with subsequent identification of the bound target cells. Most preferably, the washing step removes from the solid substrate all components of the sample that are not specifically bound by the specific binding agent.

Optically Identifying

A target cell that is bound to the solid substrate may be identified by any suitable means, preferably by optical methods. Light microscopes are relatively inexpensive, widely available, and technically simple to use, and thus one preferred optical method to detect a target cell is light microscopy. Another preferred optical method to detect a target cell is by use of a charge-coupled device (CCD), such as a CCD-equipped camera. Detecting a target cell may be achieved manually by observation of each sample by an individual capable of carrying out the method of the invention, or may be automated by means of an optical detection device coupled to a computer equipped with appropriate software for image analysis and target cell detection.

Optically identifying a target cell may be enhanced or facilitated by the use of dyes or stains that aid in distinguishing the target cell from other cells. Dyes include but are not limited to visible dyes and fluorescent dyes, such as histological dyes. Stains include enzymatic stains that produce a visible change in appearance of a cell, such as a stain for peroxidase or for alkaline phosphatase. Dyes or stains may optionally indicate cell viability or metabolic condition. The amount of dye or stain retained by the target cells bound by the specific binding agent to the solid substrate may optionally be measured, directly (for example, by spectroscopic scanning of the solid substrate) or indirectly (for example, by spectroscopic or chromatographic analysis of the dye or stain content of the target cells), and may further be used as a quantitative or semi-quantitative measurement of the number of target cells bound to the solid substrate. Where the target cell is a lymphocyte, such as a $CD4^+$ T-lymphocyte, a stain used in the method of the invention is preferably a stain that specifically distinguishes lymphocytes from other blood cells. Optionally, target cells bound to the solid substrate may be preserved for future reference. For example, target cells bound to a glass slide according to the method of the invention may be optionally dehydrated and fixed using a fixative, and stored as a permanent record of the sample.

The method of the invention can further include the step of quantifying the target cells bound to the solid substrate. Such quantification may preferably be used to calculate the absolute number of the target cell in a given volume of sample. For example, the method of the invention may be used to detect and quantify $CD4^+$ T-lymphocytes in a sample of untreated or substantially untreated whole blood, and the raw cell count obtained by the method of the invention may be used to calculate the absolute number of $CD4^+$ T-lymphocytes (as cells per microliter) in the sample of whole blood. Most preferably, the method can have an accuracy of detection and quantification of a target cell bound to the solid substrate that correlates with detection and quantification of the same target cell by flow cytometric detection. Preferably the correlation between cell counts obtained by a method of the invention and cell counts obtained by flow cytometry has a high coefficient of correlation, for example, a linear correlation with a Pearson correlation coefficient preferably of at least 0.7, more preferably of at least 0.8, and most preferably of at least 0.9. The method of the invention offers the advantage of a direct estimate of an absolute target cell count, such as an absolute $CD4^+$ T-lymphocyte count, without the need for an additional platform of technology (such as conventional hematology analyzer), and without the expense and technical requirements of flow cytometry, either alone or in combination with a conventional hematology analyzer.

II. Kit for Detecting a Target Cell

The present invention provides a kit for detecting a target cell in a sample of untreated or substantially untreated whole blood by the method of the present invention. The kit includes a solid substrate comprising: a) a multi-layered composition comprising polyanion layers and polycation layers in an alternating arrangement parallel to the surface of the solid substrate; b) a high affinity binding pair; and c) a specific binding agent that specifically binds the target cell and is bound to the solid substrate by a non-covalent binding reaction. The kit uses optical detection to detect a target cell.

Target Cell

The target cell to be detected by the kit of the invention may be any target cell of interest that is found in whole blood. Suitable target cells include erythrocytes, lymphocytes (including B-lymphocytes, T-lymphocytes, and natural killer lymphocytes), monocytes, megakaryocytes, granulocytes (including neutrophils, eosinophils, and basophils), hematopoietic stem cells, hematopoietic progenitor cells, dendritic cells, Langerhans cells, epithelial cells, fibroblasts, metastatic cancer cells, and circulating fetal cells. More preferably, a target cell may be a $CD4^+$ T-lymphocyte, a $CD8^+$ T-lymphocyte, a $CD3^+$ T-lymphocyte, a $CD19^+$ B-lymphocyte, a $CD23^+$ B-lymphocyte, a $CD25^+$ T-lymphocyte, a $CD56^+$ natural killer lymphocyte, a $CD65^+$ lymphocyte, or a $CD34^+$ hematopoietic progenitor cell.

Whole Blood

The sample of whole blood suspected of containing a target cell is untreated or substantially untreated whole blood. The kit of the present invention does not require the sample to undergo additional substantial preparation steps (such as, but not limited to, erythrocyte lysis, cell concentration, centrifugation, filtration, buffy coat preparation, plasma removal, serum removal, or isolation of a group of cells) before analysis. "Substantially untreated whole blood" refers to whole blood that has not been subjected to one or more of the following treatments: erythrocyte lysis, cell concentration, centrifugation, filtration, buffy coat preparation, plasma removal, serum removal, or isolation of a group of cells (such as isolation of leukocytes from whole blood). "Substantially untreated whole blood" may be treated with an anticoagulant, such as an EDTA salt, a citrate salt, or heparin. "Substantially untreated whole blood" may for convenience be diluted with a suitable diluent that does not substantially alter cell counts (including cell counts of erythrocytes or of white blood cells), such as sterile saline, for example when it is desirable to decrease sample viscosity or to facilitate handling of very small volumes of sample. The sample of substantially untreated whole blood may optionally have added to it one or more accessory reagents that do not interfere with the binding of a target cell to the solid substrate, do not substantially alter the cells (including erythrocytes and white blood cells) in the whole blood, and do not substantially alter the accuracy of a method of the invention (for example, as indicated by correlation of cell counts obtained by a method of the invention with cell counts obtained by flow cytometric methods). The sample of untreated whole blood may also be used directly, for example, used directly from a whole blood collection device (such as a needle and syringe or a lancet) or dropped directly onto the solid substrate (such as from a finger puncture), without treatment with an anticoagulant or without dilution. Preferably, the sample of whole blood may be analyzed by the kit of the invention within a relatively short period of time (within about six hours) after the sample is collected. Preferably, the sample of whole blood need not be refrigerated or otherwise chilled.

Solid Substrate

The solid substrate of kit of the invention can be substantially optically transparent, at least in the area of the substrate where bound target cells are to be detected by the kit of the invention. The solid substrate can be glass, quartz, silicon, silica oxides, ceramics, polymeric plastics, cycloolefins and copolymers thereof, cellulose polymers, metals, or composites made up of a combination of these materials. Glass includes silicate glass, silica carbonate glass, soda lime silica glass, as well as non-silicon-based glasses such as polymeric glasses. Polymeric plastics include but are not limited to polystyrenes, polypropylenes, polyolefins, polycarbonates, polyacrylamides, polyacrylates, polynitriles, polyurethanes, polyesters, polyethers, polyphenylenes, silicones, fluorocarbons, and the like. Polymeric plastics may include linear, branched, and substituted polymers. Polymers may also be derived from biological substances, such as cellulose and other polysaccharides, silk and other polypeptides, and latex and other natural rubbers. Cellulose polymers include for example cellulose acetates, cellulose esters, and cellulose nitrates. All of these materials may be used singly or in combination as composites, for example, in combination as mixed polymers such as a polyamide-polyethylene copolymer, or in combination as composites such as plastic-coated glass laminates. The solid substrate may be further treated in order to modify its surface. For example, the solid substrate may be cleaned, chemically or electrostatically activated, etched, textured, smoothened, or otherwise modified in order to improve its performance in the kit of the present invention.

In one embodiment of the invention, the solid substrate of the kit is preferably optically transparent. This may be advantageous, for example, when detection of the target cell is by means of a simple or compound light microscope. The solid substrate may be optically transparent in some areas and non-optically transparent in other areas, for example, a slide that is opaque in some areas and optically transparent in other areas. In other embodiments of the invention, non-optically transparent solid substrates may also be used, for example, when the target cell is detectable by optical wavelengths reflecting off the solid substrate.

In one aspect of the invention, the solid substrate of the kit comprises a substantially planar surface. The substantially planar surface need not be perfectly flat and may be flexible. Examples of substantially planar surfaces include but are not limited to glass slides, chips made out of glass (such as glass cover slips) or of other suitable materials such as quartz or plastic polymers, the bottom surface of a well (such as a well in a multi-well plate), nonporous films or membranes, porous films or membranes, filters, meshes, or grids. The solid substrate may be of any shape, including square, rectangular, round, ovoid, or irregular or shape, that is convenient for a particular application. The size of the solid substrate may be any size that is convenient for a particular application, preferably a size that enhances or optimizes efficient and cost-effective detection of a target cell. Factors that may be considered in the design of the solid substrate include, but are not limited, to the type and relative abundance of a target cell in the sample, the nature of the binding interaction between the specific binding agent and the target cell, the costs of the reagents and of manufacturing the solid substrate, and ease and efficiency of operation.

In another aspect of the invention, the solid substrate of the kit comprises a chamber. Such a chamber may be of predetermined dimensions, to hold a predetermined volume of sample. The volume of sample is selected to preferably give a sufficient volume for an accurate detection and optional quantification of a target cell, such as from about 1 nanoliter to about 100,000 microliters, or from about 1 microliter to about 1000 microliters, or from about 1 microliter to 20 microliters. The dimensions of the chamber may be of any dimensions necessary to hold the volume of sample, either as a single aliquot or as a flow-through sample with a volume that is larger than the chamber's volume. The dimensions of the chamber may permit it to hold from about 1 nanoliter to about 100,000 microliters, or from about 1 microliter to about 1000 microliters, or from about 1 microliter to 20 microliters. Preferably, the dimensions of the chamber are selected to enhance or optimize efficient and cost-effective detection of a target cell. The chamber may be of any shape or size suitable to assaying a particular target cell, and need not be enclosed on all sides. One embodiment includes a glass slide that has on one surface a concave depression of sufficient depth to contain a liquid within the depression. A chamber formed by such a depression may be optionally further enclosed, for example, by placing a cover slip over the chamber. A chamber formed by such a depression may be manufactured to hold a predetermined volume of sample. The chamber may be elongated, such as a chamber formed by a tubular or cylindrical structure. The chamber may have one or more dimensions that is relatively small or that is relatively large, such as in a capillary tube. The chamber may hold a predetermined volume of sample that is introduced into the chamber as a single aliquot. It is also possible to flow a volume of sample through the chamber that is larger than the chamber's volume. The chamber may be fitted with an inlet and with an outlet, such as with an inlet tube and with an outlet tube.

The solid substrate of the kit may also include a pattern of predetermined dimensions. Such a pattern may be of a grid, a checkerboard, concentric circles, or any pattern useful in detecting and optionally quantifying target cells bound to the solid substrate. For example, the pattern selected may have marks, such as lines forming a grid or checkerboard, delineating areas, preferably discrete areas of from about 0.0025 square millimeters to about 1 square millimeters, or from about 0.0025 square millimeters to about 0.1 square millimeters, or from about 0.0025 square millimeters to about 0.04 square millimeters. One embodiment of a substrate comprising a pattern of predetermined dimensions is a glass slide that has on one surface a chamber consisting of a concave depression of sufficient depth to contain a liquid within the depression, and that has a grid pattern printed, etched, or otherwise visibly marked on or projected onto the glass slide, particularly in the area of the chamber. In another embodiment, a pattern of predetermined dimensions is located on a separate reference slide, which may be used in conjunction with a second glass slide that has on one surface a chamber. When the two slides are aligned, the chamber and the grid pattern visually overlap, at least in part, thus visually dividing the chamber into discrete areas for convenience of an observer in detecting cells bound to the chamber. In such a case, the kit of the invention may provide a reusable reference slide.

Multi-Layered Composition Including a Specific Binding Agent

The multi-layered composition of the kit of the present invention comprises polyanion layers and polycation layers in an alternating arrangement that is substantially parallel to the surface of the solid substrate. The multi-layered composition may comprise one or more polyanion layer, and one or more polycation layer. Preferably, the multi-layered composition comprises at least three polyionic (polyanionic or polycationic in an alternating arrangement) layers. The multi-layered composition may comprise up to about 5 polyionic layers, or up to about 10 polyionic layers, or up to about 30 polyionic layers. Each polyanion layer may be the same or different as another polyanion layer. Each polycation layer may be the same or different as another polycation layer. The first layer adjacent to the surface of the solid substrate may be a polyanionic layer or a polycationic layer. Each polyanion layer is believed to be bound to each adjacent polycation layer primarily by electrostatic forces; however, applicants do not intend to be limited to such a proposed mechanism.

Each polyionic layer may comprise monomeric compounds bearing the same charge, or polymeric compounds bearing the same charge, or a combination of monomers and polymers all bearing the same charge. A polyanionic layer may comprise one or more monomeric compounds bearing one or more negative charges, or one or more polymeric compounds bearing multiple negative charges, or a combination of negatively charged monomers and polymers. A polycationic layer may comprise one or more monomeric compounds bearing one or more positive charges, or one or more polymeric compounds bearing multiple positive charges, or a combination of positively charged monomers and polymers. In an alternative embodiment, a polyionic layer may comprise amphiphilic monomers or amphiphilic polymers or a combination thereof. See, generally, U.S. Pat. No. 5,208,111, issued May 4, 1993, to Decher et al., which is herein incorporated in its entirety.

Suitable polyanions that may be used in the kit of the invention include polyphosphorus acids (for example, polyphosphoric, polyphosphonic, and polyphosphinic acids), polysulfur acids (for example, polysulfuric acids, polysulfonic acids, polysulfinic acids, polysulfenic acids, polysulfanilic acids, polysulfamidic acids, and polysulfamic acids), polyboric acids, polysilicic acids, polycarboxylic acids, anionic polyaminoacids, anionic polypeptides, anionic polyols, anionic polythiols, anionic polyimides, and combinations thereof. Anionic monomers of the above polyanions may optionally also be used. Suitable polycations that may be used in the kit of the invention include polyamines (for example, chitin, chitosan, glucosamine, poly-ornithine, and the like), polyaminiums, polyammoniums, polyphosphoniums, polyyliums, polyoxoniums, cationic polyols, cationic polythiols, cationic polyaminoacids (such as poly-lysine and poly-arginine), cationic polyaldehydes, and combinations thereof. Cationic monomers of the above polycations may optionally also be used. The polyionic (polycationic or polyanionic) layers may be derived from commercially available reagents, thus avoiding the need for chemical synthesis.

The solid substrate itself may, if suitably charged, act in effect as a foundation polyionic layer; for example, when the solid substrate is a silica glass that has been treated with a strong alkali solution (such as a strong sodium hydroxide or potassium hydroxide solution), or when the solid substrate is treated in a manner that ionizes the surface (such as by treatment with high voltage or plasma or appropriate chemical modification), or when the solid substrate has a naturally ionized surface (as occus, for example, in mica, certain ceramics, and certain biologically derived polymers).

The multi-layered composition of the kit of the present invention further includes a specific binding agent that specifically binds the target cell of interest. The specific binding agent may be located on one or more loci on the solid support. For example, the specific binding agent may be located on or more chambers on a single glass slide, or on the bottoms of one or more wells in a multi-well plate. The specific binding agent may be an intact antibody, such as a polyclonal or a monoclonal antibody. The specific binding agent may be an antibody fragment, such as an antigen-binding fragment or Fab, or an $F(ab')_2$ fragment, or the antigen-binding site of an antibody (such as a complementarity-determining region of an antibody). In some embodiments, the specific binding agent is preferably a purified, high affinity monoclonal antibody that specifically binds the target cell of interest. The specific binding agent may in other embodiments be an antigen, a ligand, or a receptor. The specific binding agent may bind to more than one type of cell, but preferably binds only one type of target cell that is found in a sample of whole blood. The specific binding agent may be comprised of more than one reagent; for example, the specific binding agent may comprise more than one type of monoclonal antibody or antibody fragment, each of which specifically binds the same type of target cell.

The multi-layered composition may further include a high affinity binding pair that serves to attach the specific binding agent to the solid substrate by a non-covalent binding reaction. Suitable high affinity binding pairs include avidin and biotin, any protein that binds an immunoglobulin, and a ligand-receptor pair. Avidin includes avidin, modified avidin (such as deglycosylated avidin), streptavidin, and derivatives thereof, which bind biotin or its derivatives with high affinity. Proteins that bind an immunoglobulin include protein A, protein G, and protein L, and can be selected for their immunoglobulin specificity. Examples of ligand-receptor pairs that can serve as a high affinity binding pair include a small molecule and a macromolecule that binds the small molecule (for example, folic acid and a folate binding protein), and an antigen-antibody pair or hapten-antibody pair (for example, nitrophenol and anti-nitrophenol antibody).

The high affinity binding pair may be used to attach the specific binding agent to the solid substrate by either of two techniques. In the first technique, the first member of the high affinity binding pair is affixed to the multi-layered composition, preferably to the top polyionic layer of the multi-layered composition, and preferably by a covalent bond. The second member of the high affinity binding pair is affixed to the specific binding agent, preferably in a manner that does not change the ability of the specific binding agent to bind to the target cell, and preferably by a covalent bond. When affixing either or both members of the high affinity binding pair, the use of a linking arm may be desirable, for example to provide sufficient flexibility for the specific binding agent to bind the target cell.

In the second technique, the high affinity binding pair is characterized by multivalency. For example, avidin and its homologues are capable of binding up to four molar equivalents of biotin. In this second technique, one unit of the first member (for example, biotin) of the high affinity binding pair is affixed to the multi-layered composition, preferably to the top polyionic layer of the multi-layered composition, and preferably by a covalent bond. A second unit of the first member of the high affinity binding pair is affixed to the specific binding agent, preferably in a manner that does not change the ability of the specific binding agent to bind to the target cell, and preferably by a covalent bond. The two units of the first member of the binding pair both bind to the second member (for example, avidin) of the high affinity binding pair, thus attaching the specific binding agent to the solid substrate by a non-covalent bond. When affixing either or both members of the high affinity binding pair, the use of a linking arm may be desirable, for example to provide sufficient flexibility for the specific binding agent to bind the target cell.

Means for Providing a Sample

The kit of the present invention may include means for providing a sample of untreated or substantially untreated whole blood. A sample of whole blood may be collected from a subject by any suitable means. In clinical settings, whole blood is conventionally collected by aseptic venipuncture, aseptic finger puncture, or other aseptic skin puncture. Suitable means for providing a sample of untreated or substantially untreated whole blood include partial-vacuum blood collection containers such as a Vacutainer® or a Monovette®, a needle and syringe, or a lancet. Optionally, suitable means may include materials, such as gloves and other personal safety equipment, biohazard disposal containers, or decontamination materials, that aid in the safe handling of potentially hazardous samples.

Means for Contacting Sample to Solid Substrate

The kit of the present invention may include means for contacting a sample of untreated or substantially untreated whole blood with the solid substrate of the kit. Suitable means can include a pipette, a capillary, a syringe, tubing, a pump, or a dropper. Optionally, suitable means may include materials, such as gloves and other personal safety equipment, biohazard disposal containers, or decontamination materials, that aid in the safe handling of potentially hazardous samples.

Means for Washing Solid Substrate

The kit of the present invention may include means for washing the solid substrate of the kit. Suitable means can include one or more wash solutions such as sterile saline, phosphate-buffered saline, or an isotonic aqueous solution. Wash solutions may optionally contain a preservative, a detergent, a surfactant, a disinfectant, an antiseptic, or other ingredients. Suitable means can include devices for contacting a wash solution with the solid substrate. Examples of such devices include pipettes, wash bottles, spray bottles, droppers, or immersion containers. Preferably, the washing means effectively removes unbound components of the sample from the solid substrate, but does not substantially remove target cells bound by the specific binding agent to the solid substrate, nor interferes with subsequent identification of the bound target cells. Most preferably, the washing means removes from the solid substrate all components of the sample that are not specifically bound by the specific binding agent. Optionally, suitable means may include materials, such as gloves and other personal safety equipment, biohazard disposal containers, or decontamination materials, that aid in the safe handling of potentially hazardous samples.

Means for Staining Bound Target Cells

The kit of the present invention may include means for staining target cells bound to the solid substrate of the kit. Such means will depend on the specific target cell to be detected. Suitable means can include dyes or stains that aid in distinguishing the target cell from other cells. Dyes include but are not limited to visible dyes and fluorescent dyes, such as histological dyes. Stains include enzymatic stains that produce a visible change in appearance of a cell, such as a stain for peroxidase or for alkaline phosphatase. Dyes or stains may optionally indicate cell viability or metabolic condition. The amount of dye or stain retained by the target cells bound by the specific binding agent to the solid substrate may optionally be measured, directly (for example, by spectroscopic scanning of the solid substrate) or indirectly (for example, by spectroscopic or chromatographic analysis of the dye or stain content of the target cells), and may further be used as a quantitative or semi-quantitative measurement of the number of target cells bound to the solid substrate. Where the target cell is a lymphocyte, such as a $CD4^+$ T-lymphocyte, a stain used in the kit of the invention is preferably a stain that specifically distinguishes lymphocytes from other blood cells. Optionally, target cells bound to the solid substrate may be preserved for future reference. For example, target cells bound to a glass slide of a kit of the invention may be optionally dehydrated and fixed using a fixative, and stored as a permanent record of the sample. Materials that are needed for optional preservation may also be included in the kit.

Instructions for Use

The kit of the invention may include instructions for the use of the kit. Such instructions may be in the form of a brochure, leaflet, pamphlet, booklet, or audiovisual materials. Preferably the instructions are sufficiently detailed to permit a user of the kit to successfully use the kit to identify, and optionally to quantify, a target cell present in a sample of untreated or substantially untreated whole blood. Such instructions may include instructions for mixing reagents, manipulating components of the kit, proper handling of a sample, and optionally calculating absolute cell counts, guidance in safety measures and in interpreting results, and trouble-shooting instructions.

EXAMPLES

Example 1

Manufacture of a Solid Substrate Comprising a Multi-Layered Composition Comprising a Specific Binding Agent that Specifically Binds a Target Cell The following example describes one method of making a solid substrate for detecting $CD4^+$ T-lymphocytes in untreated or substantially untreated whole blood.

Preliminary acid-washing. A glass microscope slide was used as an optically transparent, solid substrate. The slide measured 25.4 millimeters wide, 76.2 millimeters long, and 1.2 millimeters thick, and had a chamber consisting of a single circular concavity of from 0.4 to 0.6 millimeters depth and from 13 to 15 millimeters diameter. Other sizes of slides and chambers may be used. For example, one may use a slide with a chamber of 10 millimeters diameter, which can be used with a smaller sample volume, such as 5 microliters. The slide was soaked for two hours in a chromic acid cleaning solution (200 grams potassium dichromate in 200 milliliters distilled water and 2000 milliliters sulfuric acid). The chromic acid cleaned slide was washed with distilled water 10 times. The slide was incubated for 90 minutes in an aqueous 5% nitric acid solution at 85 degrees Celsius, and washed again with distilled water 10 times. Slides acid-washed as above may be stored in distilled water prior to further processing.

Polymer solution treatments. All incubations in polymer solutions were carried out in a humidified compartment at room temperature, with each incubation followed by rinsing 10 times in distilled water and drying under nitrogen gas. A glass slide that was acid-washed as above was subjected to the following treatments in the order given: 30 minutes in an aqueous polyethyleneimine (PEI, catalogue number 18,197-8, Aldrich Chemical Company, Inc., Milwaukee, Wis., USA) solution (20 milligrams per milliliter); 20 minutes in a solution of polystyrene sulfonate sodium salt (PSS, catalogue number 222271000, Acros Organics, Geel, Belgium) (20 milligrams per milliliter in 2 molar aqueous sodium chloride); and 20 minutes in a poly-L-lysine (PLL, catalogue number P2636, Sigma Chemical Company, St. Louis, Mo., USA) solution (20 milligrams per milliliter in 2 molar aqueous sodium chloride). These treatments resulted in the formation of a multi-layered compositions made up of three layers believed to be bound to each other by electrostatic forces: one layer each of two different polycations (polyethyleneimine and poly-L-lysine) and one layer of a polyanion (polystyrene sulfonate sodium salt) interspersed between the two polycation layers.

Antibody coating. The chamber of the dry, polymer-treated slide was treated for 5-6 hours in a humidified compartment at room temperature with 60 microliters of a biotin N-hydroxysuccinimide (catalogue number H1759, Sigma Chemical Company, St. Louis, Mo., USA) solution (5 milligrams per milliliter in dimethylformamide (catalogue number 99-10-01, Shanghai Chemical Reagent Co., Ltd., Shanghai, China) containing 1% (volume/volume) triethylamine (catalogue number 000-80142, Kishida Chemical Co., Ltd., Osaka, Japan)), rinsed 10 times with distilled water, and dried under nitrogen gas. This resulted in biotin covalently bonded to the top (poly-L-lysine) polyionic layer of the multi-layered composition. The chamber was treated for 30 minutes in a humidified compartment at room temperature with 80 microliters of a streptavidin (catalogue number SA5000, Vector Laboratories, Inc., Burlingame, Calif., USA) solution (50 micrograms per milliliter in 150 millimolar phosphate-buffered saline, pH 7.2 (PBS)), and rinsed 10 times with PBS. The chamber was treated for 40 minutes in a humidified compartment at room temperature with 50 microliters of a biotinylated anti-human CD4 monoclonal antibody solution (Immunotech clone 13B8.2, catalogue number IM 0704, Beckman Coulter, Inc., Fullerton, Calif., USA) (5 micrograms per milliliter in PBS), and rinsed 10 times with PBS. The biotin unit that labels the antibody is in this example covalently bonded to the antibody, but this need not be the case. The antibody was thus attached to the slide by a non-covalent binding reaction that may be represented thus:

(antibody)-biotin:::streptavidin:::biotin-(solid substrate).

This example of a substrate comprising a multi-layered composition comprising a specific binding agent may be more fully represented thus:

(antibody)-biotin:::streptavidin:::biotin-(PLL:::PSS:::PEI:::glass).

The slide was stored at 4 degrees Celsium in a bovine serum albumin (catalogue number A7906, Sigma Chemical Company, St. Louis, Mo., USA) solution (1 milligram per milliliter in PBS containing 0.2% (weight/volume) sodium azide (catalogue number S8032, Sigma Chemical Company, St. Louis, Mo., USA)) prior to use in assays.

Example 2

Optimization of Reagent Conditions Using Fluorescence Emission

The following example describes the determination of optimal concentrations of reagent solutions using a fluorescence emission method. Unless otherwise specified, all reagent sources were the same as those in Example 1.

Polyethyleneimine and polystyrene sulfonate sodium salt concentrations. Glass slides are acid-washed as described in Example 1. All incubations in polymer solutions were carried out at 25 degrees Celsius and 40% humidity, with each incubation followed by rinsing 10 times in distilled water and drying under nitrogen gas. Individual slides were subjected to the following treatments in the order given: 30 minutes in an aqueous polyethyleneimine (PEI) solution (at a concentration of 0.2, 2, 20, or 200 milligrams per milliliter); 20 minutes in a solution of polystyrene sulfonate sodium salt (PSS) (at a concentration of 0.2, 2, 20, or 200 milligrams per milliliter in 2 molar aqueous sodium chloride); and 20 minutes in a solution of poly-L-lysine (PLL) labeled with fluorescein isothiocyanate (PLL-FITC, catalogue number P3069, Sigma Chemical Company, St. Louis, Mo., USA) (2 milligrams per milliliter in 2 molar aqueous sodium chloride). The slides were placed on an ultraviolet transilluminator and irradiated at 480 nanometers, and the relative fluorescence emission intensity was measured at 520 nanometers using a charge-coupled device (CCD) camera. The results are given in Table 1.

TABLE 1

| concentration (milligrams per milliliter) | | | relative fluorescence emission intensity (520 nm) |
|---|---|---|---|
| polyethyleneimine | polystyrene sulfonate sodium salt | poly-L-lysine (labeled with fluorescein isothiocyanate) | |
| 0 | 0 | 2 | 79.57 |
| 0.2 | 0.2 | 2 | 72.72 |
| 2 | 2 | 2 | 93.09 |
| 20 | 20 | 2 | 99.38 |
| 200 | 200 | 2 | 98.42 |

Poly-L-lysine concentration. Glass slides are acid-washed as described in Example 1. All incubations in polymer solutions were carried out at 25 degrees Celsius and 40% humidity, with each incubation followed by rinsing 10 times in distilled water and drying under nitrogen gas. Individual slides were subjected to the following treatments in the order given: 30 minutes in an aqueous polyethyleneimine (PEI) solution (20 milligrams per milliliter); 20 minutes in a solution of polystyrene sulfonate sodium salt (PSS) (20 milligrams per milliliter in 2 molar aqueous sodium chloride); and 20 minutes in a solution of poly-L-lysine (PLL) (at a concentration of 0.1, 2, 20, or 200 milligrams per milliliter in 2 molar aqueous sodium chloride). Slides thus polymer-treated were incubated for 5-6 hours at 25 degrees Celsius and 40% humidity in a biotin N-hydroxysuccinimide solution (20 milligrams per milliliter in dimethylformamide containing 1% (volume/volume) triethylamine), rinsed 10 times with distilled water, and dried under nitrogen gas. Slides thus biotinylated were incubated for 30 minutes at 25 degrees Celsius and 40% humidity in a solution of streptavidin labeled with fluorescein isothiocyanate (catalogue number SA5001, Vector Laboratories, Inc., Burlingame, Calif., USA) (100 micrograms per milliliter in 150 millimolar phosphate-buffered saline, pH 7.2 (PBS)), and rinsed 10 times with PBS. The slides were placed on an ultraviolet transilluminator and irradiated at 480 nanometers, and the relative fluorescence emission intensity was measured at 520 nanometers using a charge-coupled device (CCD) camera. The results are given in Table 2.

40% humidity, with each incubation followed by rinsing 10 times in distilled water and drying under nitrogen gas. Individual slides were subjected to the following treatments in the order given: 30 minutes in an aqueous polyethyleneimine (PEI) solution (20 milligrams per milliliter); 20 minutes in a solution of polystyrene sulfonate sodium salt (PSS) (20 milligrams per milliliter in 2 molar aqueous sodium chloride); and 20 minutes in a solution of poly-L-lysine (PLL) (20 milligrams per milliliter in 2 molar aqueous sodium chloride). Slides thus polymer-treated were incubated for 5-6 hours at 25 degrees Celsius and 40% humidity in a biotin N-hydroxysuccinimide solution (at a concentration of 1, 5, 10, 20, or 40 milligrams per milliliter in dimethylformamide containing 1% (volume/volume) triethylamine), rinsed 10 times with distilled water, and dried under nitrogen gas. Slides thus biotinylated were incubated for 30 minutes at 25 degrees Celsius and 40% humidity in a solution of streptavidin labeled with fluorescein isothiocyanate (catalogue number SA5001, Vector Laboratories, Inc., Burlingame, Calif., USA) (100 micrograms per milliliter in 150 millimolar phosphate-buffered saline, pH 7.2 (PBS)), and rinsed 10 times with PBS. The slides were placed on an ultraviolet transilluminator and irradiated at 480 nanometers, and the relative fluorescence

TABLE 2

| concentration (milligrams per milliliter) | | | | | relative fluorescence emission intensity (520 nm) |
| --- | --- | --- | --- | --- | --- |
| polyethyleneimine | polystyrene sulfonate sodium salt | poly-L-lysine | biotin N-hydroxysuccinimide | streptavidin (labeled with fluorescein isothiocyanate) | |
| 20 | 20 | 0 | 20 | 100 | 60.09 |
| 20 | 20 | 0.2 | 20 | 100 | 64.83 |
| 20 | 20 | 2 | 20 | 100 | 77.75 |
| 20 | 20 | 20 | 20 | 100 | 94.32 |
| 20 | 20 | 200 | 20 | 100 | 92.21 |

Biotin N-hydroxysuccinimide concentration. Glass slides are acid-washed as described in Example 1. All incubations in polymer solutions were carried out at 25 degrees Celsius and emission intensity was measured at 520 nanometers using a charge-coupled device (CCD) camera. The results are given in Table 3.

TABLE 3

| concentration (milligrams per milliliter) | | | | | relative fluorescence emission intensity (520 nm) |
|---|---|---|---|---|---|
| polyethyleneimine | polystyrene sulfonate sodium salt | poly-L-lysine | biotin N-hydroxysuccinimide | streptavidin (labeled with fluorescein isothiocyanate) | |
| 20 | 20 | 20 | 0 | 0.100 | 83.86 |
| 20 | 20 | 20 | 1 | 0.100 | 104.91 |
| 20 | 20 | 20 | 5 | 0.100 | 115.8 |
| 20 | 20 | 20 | 10 | 0.100 | 107.25 |
| 20 | 20 | 20 | 20 | 0.100 | 106.81 |
| 20 | 20 | 20 | 40 | 0.100 | 89.78 |

Biotin N-hydroxysuccinimide reaction time. Glass slides are acid-washed as described in Example 1. All incubations in polymer solutions were carried out at 25 degrees Celsius and 40% humidity, with each incubation followed by rinsing 10 times in distilled water and drying under nitrogen gas. Individual slides were subjected to the following treatments in the order given: 30 minutes in an aqueous polyethyleneimine (PEI) solution (20 milligrams per milliliter); 20 minutes in a solution of polystyrene sulfonate sodium salt (PSS) (20 milligrams per milliliter in 2 molar aqueous sodium chloride); and 20 minutes in a solution of poly-L-lysine (PLL) (20 milligrams per milliliter in 2 molar aqueous sodium chloride). Slides thus polymer-treated were incubated for 2, 5.5, or 20 hours at 25 degrees Celsius and 40% humidity in a biotin N-hydroxysuccinimide solution (5 milligrams per milliliter in dimethylformamide containing 1% (volume/volume) triethylamine), rinsed 10 times with distilled water, and dried under nitrogen gas. Slides thus biotinylated were incubated for 30 minutes at 25 degrees Celsius and 40% humidity in a solution of streptavidin labeled with fluorescein isothiocyanate (catalogue number SA5001, Vector Laboratories, Inc., Burlingame, Calif., USA) (100 micrograms per milliliter in 150 millimolar phosphate-buffered saline, pH 7.2. (PBS)), and rinsed 10 times with PBS. The slides were placed on an ultraviolet transilluminator and irradiated at 480 nanometers, and the relative fluorescence emission intensity was measured at 520 nanometers using a charge-coupled device (CCD) camera. The results are given in Table 4.

TABLE 4

| Biotin N-hydroxysuccinimide reaction time (hours) | relative fluorescence emission intensity (520 nm) |
|---|---|
| 2 | 89.77 |
| 5.5 | 102.7 |
| 20 | 93.33 |

Streptavidin concentration. Glass slides are acid-washed as described in Example 1. All incubations in polymer solutions were carried out at 25 degrees Celsius and 40% humidity, with each incubation followed by rinsing 10 times in distilled water and drying under nitrogen gas. Individual slides were subjected to the following treatments in the order given: 30 minutes in an aqueous polyethyleneimine (PEI) solution (20 milligrams per milliliter); 20 minutes in a solution of polystyrene sulfonate sodium salt (PSS) (20 milligrams per milliliter in 2 molar aqueous sodium chloride); and 20 minutes in a solution of poly-L-lysine (PLL) (20 milligrams per milliliter in 2 molar aqueous sodium chloride). Slides thus polymer-treated were incubated for 5-6 hours at 25 degrees Celsius and 40% humidity in a biotin N-hydroxysuccinimide solution (5 milligrams per milliliter in dimethylformamide containing 1% (volume/volume) triethylamine), rinsed 10 times with distilled water, and dried under nitrogen gas. Slides thus biotinylated were incubated for 30 minutes at 25 degrees Celsius and 40% humidity in a solution of streptavidin labeled with fluorescein isothiocyanate (catalogue number SA5001, Vector Laboratories, Inc., Burlingame, Calif., USA) (at a concentration of 10, 25, 50, or 100 micrograms per milliliter in 150 millimolar phosphate-buffered saline, pH 7.2 (PBS)), and rinsed 10 times with PBS. The slides were placed on an ultraviolet transilluminator and irradiated at 480 nanometers, and the relative fluorescence emission intensity was measured at 520 nanometers using a charge-coupled device (CCD) camera. The results are given in Table 5.

TABLE 5

| concentration (milligrams per milliliter) | | | | | relative fluorescence emission intensity (520 nm) |
|---|---|---|---|---|---|
| polyethyleneimine | polystyrene sulfonate sodium salt | poly-L-lysine | biotin N-hydroxysuccinimide | streptavidin (labeled with fluorescein isothiocyanate) | |
| 20 | 20 | 20 | 5 | 0.010 | 66.87 |
| 20 | 20 | 20 | 5 | 0.025 | 90.72 |
| 20 | 20 | 20 | 5 | 0.050 | 101.2 |
| 20 | 20 | 20 | 5 | 0.100 | 93.33 |

Example 3

Optimization of Reagent Conditions by Peroxidase Reaction

The following example describes the determination of optimal concentrations of reagent solutions using a peroxidase reaction method. Unless otherwise specified, all reagent sources were the same as those in Example 1.

Polyethyleneimine, polystyrene sulfonate sodium salt, and poly-L-lysine concentrations. Glass slides are acid-washed as described in Example 1. All incubations in polymer solutions were carried out at 18 degrees Celsius and 34% humidity, with each incubation followed by rinsing 10 times in distilled water and drying under nitrogen gas. Individual slides were subjected to the following treatments in the order given: 30 minutes in an aqueous polyethyleneimine (PEI) solution (at a concentration of 0.2, 2, 20, or 200 milligrams per milliliter); 20 minutes in a solution of polystyrene sulfonate sodium salt (PSS) (at a concentration of 0.2, 2, 20, or 200 milligrams per milliliter in 2 molar aqueous sodium chloride); and 20 minutes in a solution of poly-L-lysine (PLL) (at a concentration of 0.2, 2, 20, or 200 milligrams per milliliter in 2 molar aqueous sodium chloride). The chamber of each slide thus polymer-treated was treated for 5-6 hours at 18 degrees Celsius and 34% humidity with 60 microliters of a biotin N-hydroxysuccinimide solution (5 milligrams per milliliter in dimethylformamide containing 1% (volume/volume) triethylamine), rinsed 10 times with distilled water, and dried under nitrogen gas. The chamber of each slide thus biotinylated was treated for 30 minutes at 18 degrees Celsius and 34% humidity with 80 microliters of a streptavidin solution (50 micrograms per milliliter in 150 millimolar phosphate-buffered saline, pH 7.2 (PBS)), and rinsed 10 times with PBS. Individual chambers of slides thus streptavidinated received either 100 microliters of a solution of biotinylated horseradish peroxidase (catalogue number P9568, Sigma Chemical Company, St. Louis, Mo., USA) (10 nanograms per milliliter in PBS containing 0.05% (volume/volume) Tween-20 (catalogue number P3563, Sigma Chemical Company, St. Louis, Mo., USA)) or 100 microliters of streptavidin labeled with horseradish peroxidase (catalogue number S5512, Sigma Chemical Company, St. Louis, Mo., USA) (10 nanograms per milliliter in PBS containing 0.05% (volume/volume) Tween-20), were incubated for 30 minutes at 18 degrees Celsius and 34% humidity, and rinsed 10 times with PBS. Each chamber received 100 microliters of 3,3',5,5'-tetramethylbenzidine solution (TMB Liquid Substrate System, catalogue number T8665, Sigma Chemical Company, St. Louis, Mo., USA) and was incubated for 15 minutes at 18 degrees Celsius and 34% humidity. The enzymatic reaction was stopped by the addition of 50 microliters aqueous 0.5 molar sulfuric acid. The absorbance of the reaction mixture was measured with a UV spectrophotometer at 450 nanometers. The results are given in Table 6.

TABLE 6

| concentration (mg/mL) | | | concentration (ng/mL) | | |
|---|---|---|---|---|---|
| polyethyleneimine | polystyrene sulfonate sodium salt | poly-L-lysine | biotinylated horseradish peroxidase | streptavidin (labeled with horseradish peroxidase) | absorbance (450 nm) |
| 20 | 20 | 20 | 0 | 10 | 0.072 |
| 0.2 | 0.2 | 0.2 | 10 | 0 | 0.234 |
| 2 | 2 | 2 | 10 | 0 | 0.583 |
| 20 | 20 | 20 | 10 | 0 | 1.21 |
| 200 | 200 | 200 | 10 | 0 | 0.965 |

Biotin N-hydroxysuccinimide concentration. Glass slides are acid-washed as described in Example 1. All incubations in polymer solutions were carried out at 16 degrees Celsius and 58% humidity, and were followed by rinsing 10 times in distilled water and drying under nitrogen gas. Individual slides were subjected to the following treatments in the order given: 30 minutes in an aqueous polyethyleneimine (PEI) solution (20 milligrams per milliliter); 20 minutes in a solution of polystyrene sulfonate sodium salt (PSS) (20 milligrams per milliliter in 2 molar aqueous sodium chloride); and 20 minutes in a solution of poly-L-lysine (PLL) (20 milligrams per milliliter in 2 molar aqueous sodium chloride). The chamber of each slide thus polymer-treated was treated for 5-6 hours at 16 degrees Celsius and 58% humidity with 60 microliters of a biotin N-hydroxysuccinimide solution (5 milligrams per milliliter in dimethylformamide containing 1% (volume/volume) triethylamine), then rinsed 10 times with distilled water and dried under nitrogen gas. The chamber of each slide thus biotinylated was treated for 30 minutes at 16 degrees Celsius and 58% humidity with 80 microliters of a streptavidin solution (at a concentration of 10, 25, 50, or 100 micrograms per milliliter in 150 millimolar phosphate-buffered saline, pH 7.2 (PBS)), then rinsed 10 times with PBS. Individual chambers of slides thus streptavidinated received either 100 microliters of a solution of biotinylated horseradish peroxidase (catalogue number P9568, Sigma Chemical Company, St. Louis, Mo., USA) (10 nanograms per milliliter in PBS containing 0.05% (volume/volume) Tween-20 (catalogue number P3563, Sigma Chemical Company, St. Louis, Mo., USA)), or 100 microliters of streptavidin labeled with horseradish peroxidase (catalogue number S5512, Sigma Chemical Company, St. Louis, Mo., USA) (10 nanograms per milliliter in PBS containing 0.05% (volume/volume) Tween-20), were incubated for 30 minutes at 16 degrees Celsius and 58% humidity, and rinsed 10 times with PBS. Each chamber received 100 microliters of 3,3',5,5'-tetramethylbenzidine solution (TMB Liquid Substrate System, catalogue number T8665, Sigma, St. Louis, Mo., USA) and was incubated for 15 minutes at 16 degrees Celsius and 58% humidity. The enzymatic reaction was stopped by the addition of 50 microliters aqueous 0.5 molar sulfuric acid. The absorbance of the reaction mixture was measured with a UV spectrophotometer at 450 nanometers. The results are given in Table 7.

TABLE 7

| concentration (mg/mL) | | | | concentration (ng/mL) | | |
| --- | --- | --- | --- | --- | --- | --- |
| polyethyleneimine | polystyrene sulfonate sodium salt | poly-L-lysine | streptavidin | biotinylated horseradish peroxidase | streptavidin (labeled with horseradish peroxidase) | absorbance (450 nm) |
| 20 | 20 | 20 | 0.050 | 0 | 10 | 0.071 |
| 20 | 20 | 20 | 0.010 | 10 | 0 | 0.437 |
| 20 | 20 | 20 | 0.025 | 10 | 0 | 0.946 |
| 20 | 20 | 20 | 0.050 | 10 | 0 | 1.243 |
| 20 | 20 | 20 | 0.100 | 10 | 0 | 1.165 |

Biotin N-hydroxysuccinimide reaction time. Glass slides are acid-washed as described in Example 1. All incubations in polymer solutions were carried out at 16 degrees Celsius and 38% humidity, and were followed by rinsing 10 times in distilled water and drying under nitrogen gas. Individual slides were subjected to the following treatments in the order given: 30 minutes in an aqueous polyethyleneimine (PEI) solution (20 milligrams per milliliter); 20 minutes in a solution of polystyrene sulfonate sodium salt (PSS) (20 milligrams per milliliter in 2 molar aqueous sodium chloride); and 20 minutes in a solution of poly-L-lysine (PLL) (20 milligrams per milliliter in 2 molar aqueous sodium chloride). The chamber of each slide thus polymer-treated was treated for 2, 5.5, or 20 hours at 16 degrees Celsius and 38% humidity with 60 microliters of a biotin N-hydroxysuccinimide solution (5 milligrams per milliliter in dimethylformamide containing 1% (volume/volume) triethylamine), then rinsed 10 times with distilled water and dried under nitrogen gas. The chamber of each slide thus biotinylated was treated for 30 minutes at 16 degrees Celsius and 38% humidity with 80 microliters of a streptavidin solution (50 micrograms per milliliter in 150 millimolar phosphate-buffered saline, pH 7.2 (PBS)), then rinsed 10 times with PBS. Individual chambers of slides thus streptavidinated received either 100 microliters of a solution of biotinylated horseradish peroxidase (catalogue number P9568, Sigma Chemical Company, St. Louis, Mo., USA) (10 nanograms per milliliter in PBS containing 0.05% (volume/volume) Tween-20 (catalogue number P3563, Sigma Chemical Company, St. Louis, Mo., USA)), or 100 microliters of streptavidin labeled with horseradish peroxidase (catalogue number S5512, Sigma Chemical Company, St. Louis, Mo., USA) (10 nanograms per milliliter in PBS containing 0.05% (volume/volume) Tween-20), were incubated for 30 minutes at 16 degrees Celsius and 38% humidity, and rinsed 10 times with PBS. Each chamber received 100 microliters of 3,3',5,5'-tetramethylbenzidine solution (TMB Liquid Substrate System, catalogue number T8665, Sigma, St. Louis, Mo., USA) and was incubated for 15 minutes at 16 degrees Celsius and 38% humidity. The enzymatic reaction was stopped by the addition of 50 microliters aqueous 0.5 molar sulfuric acid. The absorbance of the reaction mixture was measured with a UV spectrophotometer at 450 nanometers. The results are given in Table 8.

TABLE 8

| | concentration (ng/mL) | | |
| --- | --- | --- | --- |
| Biotin N-hydroxysuccinimide reaction time (hours) | biotinylated horseradish peroxidase | streptavidin (labeled with horseradish peroxidase) | absorbance (450 nm) |
| 5.5 | 0 | 10 | 0.055 |
| 2 | 10 | 0 | 0.627 |
| 5.5 | 10 | 0 | 1.176 |
| 20 | 10 | 0 | 0.786 |

Example 4

A Method for Detecting a Target Cell in Untreated or Substantially Untreated Whole Blood The following describes an example of a method for detecting a target cell present in a sample of untreated or substantially untreated whole blood. Unless otherwise specified, all reagent sources were the same as those in Example 1.

Whole blood may be collected from a subject by any suitable technique, such as by aseptic venipuncture, aseptic finger puncture, or other aseptic skin puncture. Cell counts obtained by flow cytometry are generally made using whole blood collected by aseptic venipuncture. Since whole blood obtained by aseptic venipuncture differs in composition from that obtained by aseptic skin puncture techniques, cell counts using the method of the present invention, for direct comparison with flow cytometric measurements, are generally made on whole blood cells collected by aseptic venipuncture.

Whole blood used in this method is untreated or substantially untreated. The whole blood is not subjected to erythrocyte lysis, concentration, centrifugation, filtration, buffy coat preparation, or plasma removal. The whole blood can be diluted into saline or other suitable diluent. The volume of diluted whole blood required for this assay is very small (5 to 10 microliters), and for this reason it is convenient to use a larger volume sample of whole blood that is treated with an anticoagulant (such as an ethylenediaminetetraacetic (EDTA) salt, anticoagulant citrate dextrose (ACD), or heparin). The whole blood sample should be stored at room temperature (between 18 and 25 degrees Celsius) and processed within about 6 hours when possible. The whole blood sample should not be chilled or refrigerated.

A 1-milliliter sample of peripheral blood was obtained from a healthy volunteer by aseptic venipuncture. The whole blood was collected into a vessel containing an EDTA salt. A subsample of the whole blood was diluted 40-fold by pipetting 50 microliters of the anticoagulated whole blood into 1950 microliters of 150 millimolar phosphate-buffered saline, pH 7.2 (PBS) in a 5-milliliter tube, followed by mixing by mechanical agitation.

In this example, the target cells were $CD4^+$ T-lymphocytes. An anti-human CD4 monoclonal antibody-coated glass slide prepared as in Example 1 was used as the solid substrate in the cell count assay. The glass slide was rinsed with PBS and the slide wiped dry except for the antibody-coated chamber. Ten microliters of the 40-fold diluted whole blood sample was pipetted into the chamber and the slide incubated in a humidified compartment for 30 minutes at room temperature. The slide was rinsed 10 times with PBS. Cells bound to the chamber were stained for peroxidase and counterstained as follows. Cells bound to the chamber were incubated for 1 minute at room temperature in a few drops of a first peroxidase staining solution (0.3 grams benzidine (catalogue number Q/SJYH, Yuanhang Reagent, China) and 1 milliliter 36% sodium nitroferricyanide (catalogue number 20040414, Shanghai Chemical Reagent Co., Ltd., Shanghai, China) in 99 milliliters 95% ethanol). A few drops of a second peroxidase staining solution (0.01% aqueous hydrogen peroxide (catalogue number 098004, Shanghai Jinlu Reagent Co., Ltd., Shanghai, China)) was added, the two solutions mixed in the chamber, the cells incubated in this mixture for 4 minutes at room temperature, and the chamber rinsed with water. Cells bound to the chamber were optionally decolorized with 95% ethanol, rinsed with distilled water, and counterstained with fuchsin basic (catalogue number 71019654, Shanghai Chemical Reagent Co., Ltd., Shanghai, China). Fuchsin basic or nuclear fast red are the preferred counterstains in this example, although stains such as Wright's stain or others can be used according to the type of target cell. No second antibody was necessary nor-used for detection of the target cell.

The cell counting assay used a reference slide that had printed on its surface a pattern, consisting of a 3-by-3 grid made up of two perpendicularly intersecting pairs of lines, of predetermined dimensions and of the same planar diameter as that of the circular chamber of the antibody-coated slide. The antibody-coated slide was placed atop the reference slide, and the two slides placed horizontally on a light microscope stage, so that to an observer viewing the slides through the microscope, the circumferences of the chamber and of the grid pattern were aligned, and the chamber appeared to be divided into nine roughly equal-sized sectors. Another example of a reference slide is a slide having a 1 millimeter by 1 millimeter checkerboard pattern etched on its surface; this is useful for example with 10-fold magnification.

The pattern is for convenience of the observer in counting cells bound to the chamber. A pattern of predetermined dimensions could, alternatively, be printed, etched, or otherwise visibly marked on or projected onto the surface of the antibody-coated slide itself.

The $CD4^+$ T-lymphocytes were identified as those target cells bound to the chamber that were red-to-pink colored with fuchsin basic stain, peroxidase-negative, and lacked a black or brown grainy appearance. Non-specifically bound, non-target cells were identified as leukocytes bound to the chamber that had a black or brown grainy appearance, such as monocytes and neutrophils. $CD4^+$ T-lymphocytes were counted from each of the nine grid sectors and the nine values summed to give a total $CD4^+$ T-lymphocyte count. This number was divided by the volume in microliters of diluted blood analyzed, and multiplied by the dilution factor, as a direct measurement of the absolute cell count of $CD4^+$ T-lymphocytes per microliter of whole blood.

This example of a method for detecting a target cell present in a sample of untreated or substantially untreated whole blood may be applied using different sizes of slides and chambers. Smaller chambers use smaller volumes of sample or reagents, and may require a shorter observation time for detecting target cells bound to the solid substrate. For example, a slide with a chamber of 10 millimeters diameter was used with a smaller sample volume (5 microliters of 20-fold diluted whole blood), to give substantially the same results as those obtained with a slide with a chamber of 13 to 15 millimeters diameter used with a 10 microliter sample of 40-fold diluted whole blood. Conversely, larger chambers, larger surface area of the solid substrate (for example, where the solid substrate is substantially planar), a higher effective concentration of the specific binding agent that specifically binds the target cell of interest, or larger sample sizes may be desirable for detecting relatively rare target cells.

Example 5

Optimization of Conditions for Binding a Target Cell in Untreated or Substantially Untreated Whole Blood Unless otherwise specified, all reagent sources were the same as those in Example 1.

The following example describes the determination of optimal conditions (concentrations of reagent solutions and sample incubation time) for binding a target cell present in a sample of untreated or substantially untreated whole blood.

Polyethyleneimine, polystyrene sulfonate sodium salt, and poly-L-lysine concentrations. Cell counts were carried out using whole blood from a healthy volunteer and the procedure described in Example 4, except that the glass slides were treated with solutions of polyethyleneimine, polystyrene sulfonate sodium salt, and poly-L-lysine at concentrations of 2, 20, or 200 milligrams per milliliter. The sample of diluted whole blood was incubated in the antibody-coated chamber at 15 degrees Celsius and 32% humidity. The results are given in Table 9.

The whole blood sample was also analyzed by flow cytometry and conventional hemocytological analysis to obtain an absolute $CD4^+$ T-lymphocyte count for comparison. Cell counts by conventional hemocytological analysis were: 4800 white blood cells, 1600 total lymphocytes, 500 mixed monocytes, eosinophils, and basophils. Flow cytometry was carried out with a flow cytometer (model Bryte HS, BioRad Laboratories, Inc., Hercules, Calif., USA), equipped with a xenon laser operating at a laser period of 350 to 600 nanometers, and 520 nanometer and 570 nanometer filters (for fluorescein analysis and phycoerythrin analysis, respectively). The flow cytometer was operated with a fluoroscein sensitivity of less than 1000 MESF (molecules of equivalent soluble fluorescein), a scattered light sensitivity of 0.22 micrometers, and a differentiation rate of 0.02 micrometers. A combination CD4/CD8 fluorescent labelling reagent, consisting of fluorescein-labelled anti-human CD4 monoclonal antibody from clone 13B8.2 and phycoerythrin-labelled anti-human CD4 monoclonal antibody from clone B9.11 (Immunotech catalogue number IM 1385, Beckman Coulter, Inc., Fullerton, Calif., USA) was used to label the flow cytometry samples. By flow cytometric analysis, $CD4^+$ T-lymphocytes was measured at 34.2% of the total lymphocytes (equivalent to 547 $CD4^+$ T-lymphocytes in 1600 total lymphocytes).

TABLE 9

| Polymer concentration (mg/mL) | | | GRID | Cells counted per grid sector | | | | | | | | | Total cells in grid | Absolute CD4⁺ T-lymphocyte count, cells/μL (discrepancy from FC + H*) | CD4⁺ T-lymphocytes (% of total lymphocytes) (discrepancy from FC + H*) |
|---|---|---|---|---|---|---|---|---|---|---|---|---|---|---|---|
| PEI | PSS | PLL | SECTOR | 1 | 2 | 3 | 4 | 5 | 6 | 7 | 8 | 9 | | | |
| 2 | 2 | 2 | CD4⁺ cells | 8 | 10 | 6 | 24 | 56 | 26 | 16 | 39 | 19 | 204 | 816 | 51.0% |
| | | | Positive cells | 16 | 24 | 18 | 28 | 68 | 34 | 23 | 54 | 21 | 286 | (269) | (17.9%) |
| 20 | 20 | 20 | CD4⁺ cells | 3 | 10 | 4 | 19 | 41 | 20 | 9 | 20 | 6 | 132 | 528 | 33.0% |
| | | | Positive cells | 3 | 5 | 2 | 3 | 7 | 3 | 2 | 5 | 3 | 33 | (−19) | (−1.2%) |
| 200 | 200 | 200 | CD4⁺ cells | 3 | 10 | 4 | 13 | 35 | 7 | 5 | 18 | 3 | 98 | 392 | 24.5% |
| | | | Positive cells | 1 | 0 | 0 | 3 | 5 | 4 | 2 | 7 | 0 | 22 | (−155) | (−9.7%) |

*Values in parentheses give the discrepancy between the absolute CD4⁺ cell count or percentage, respectively, obtained by the method of the invention (in cells per microliter) from that obtained by flow cytometric CD4⁺ analysis and hemocytometric cell counts (FC + H).

Biotin N-hydroxysuccinimide concentration. Cell counts were carried out using whole blood from a healthy volunteer and the procedure described in Example 4, except that the glass slides were treated with solutions of biotin N-hydroxysuccinimide at concentrations of 1, 5, or 20 milligrams per milliliter. The sample of diluted whole blood was incubated in the antibody-coated chamber at 16 degrees Celsius and 38% humidity. The results are given in Table 10.

The whole blood sample was also analyzed by flow cytometry and conventional hemocytological analysis to obtain an absolute CD4⁺ T-lymphocyte count for comparison. Cell counts by conventional hemocytological analysis were: 5200 white blood cells, 1900 total lymphocytes, 600 mixed monocytes, eosinophils, and basophils. Flow cytometry was carried out with a flow cytometer (model Bryte HS, BioRad Laboratories, Inc., Hercules, Calif., USA), equipped with a xenon laser operating at a laser period of 350 to 600 nanometers, and 520 nanometer and 570 nanometer filters (for fluorescein analysis and phycoerythrin analysis, respectively). The flow cytometer was operated with a fluoroscein sensitivity of less than 1000 MESF (molecules of equivalent soluble fluorescein), a scattered light sensitivity of 0.22 micrometers, and a differentiation rate of 0.02 micrometers. A combination CD4/CD8 fluorescent labelling reagent, consisting of fluorescein-labelled anti-human CD4 monoclonal antibody from clone 13B8.2 and phycoerythrin-labelled anti-human CD4 monoclonal antibody from clone B9.11 (Immunotech catalogue number IM 1385, Beckman Coulter, Inc., Fullerton, Calif., USA) was used to label the flow cytometry samples. By flow cytometric analysis, CD4⁺ T-lymphocytes was measured at 33.4% of the total lymphocytes (equivalent to 634 CD4⁺ T-lymphocytes in 1900 total lymphocytes).

TABLE 10

| Biotin N-hydroxy-succinimide concentration (mg/mL) | GRID SECTOR | Cells counted per grid sector | | | | | | | | | Total cells in grid | Absolute CD4⁺ T-lymphocyte count, cells/μL (discrepancy from FC + H*) | CD4⁺ T-lymphocytes (% of total lymphocytes) (discrepancy from FC + H*) |
|---|---|---|---|---|---|---|---|---|---|---|---|---|---|
| | | 1 | 2 | 3 | 4 | 5 | 6 | 7 | 8 | 9 | | | |
| 1 | CD4⁺ cells | 11 | 24 | 13 | 21 | 65 | 19 | 13 | 32 | 17 | 215 | 860 | 45.3% |
| | Positive cells | 20 | 29 | 17 | 29 | 67 | 34 | 21 | 37 | 25 | 279 | (226) | (11.9%) |
| 5 | CD4⁺ cells | 4 | 12 | 5 | 15 | 45 | 23 | 13 | 23 | 16 | 156 | 624 | 32.8% |
| | Positive cells | 4 | 7 | 4 | 8 | 14 | 9 | 2 | 5 | 7 | 60 | (−10) | (−0.6) |
| 20 | CD4⁺ cells | 3 | 10 | 4 | 13 | 46 | 16 | 13 | 25 | 7 | 137 | 548 | 28.8% |
| | Positive cells | 0 | 3 | 0 | 5 | 9 | 3 | 5 | 5 | 2 | 32 | (−86) | (−5.6%) |

*Values in parentheses give the discrepancy between the absolute CD4⁺ cell count or percentage, respectively, obtained by the method of the invention (in cells per microliter) from that obtained by flow cytometric CD4⁺ analysis and hemocytometric cell counts (FC + H).

Streptavidin concentration. Cell counts were carried out using whole blood from a healthy volunteer and the procedure described in Example 4, except that the glass slides were treated with solutions of streptavidin at concentrations of 10, 50, or 100 micrograms per milliliter. The sample of diluted whole blood was incubated in the antibody-coated chamber at 17 degrees Celsius and 54% humidity. The results are given in Table 11.

The whole blood sample was also analyzed by flow cytometry and conventional hemocytological analysis to obtain an absolute CD4⁺ T-lymphocyte count for comparison. Cell counts by conventional hemocytological analysis were: 4900 white blood cells, 1650 total lymphocytes, 500 mixed monocytes, eosinophils, and basophils. Flow cytometry was carried out with a flow cytometer (model Bryte HS, BioRad Laboratories, Inc., Hercules, Calif., USA), equipped with a xenon laser operating at a laser period of 350 to 600 nanometers, and 520 nanometer and 570 nanometer filters (for fluorescein analysis and phycoerythrin analysis, respectively).

The flow cytometer was operated with a fluoroscein sensitivity of less than 1000 MESF (molecules of equivalent soluble fluorescein), a scattered light sensitivity of 0.22 micrometers, and a differentiation rate of 0.02 micrometers. A combination CD4/CD8 fluorescent labelling reagent, consisting of fluorescein-labelled anti-human CD4 monoclonal antibody from clone 13B8.2 and phycoerythrin-labelled anti-human CD4 monoclonal antibody from clone B9.11 (Immunotech catalogue number IM 1385, Beckman Coulter, Inc., Fullerton, Calif., USA) was used to label the flow cytometry samples. By flow cytometric analysis, $CD4^+$ T-lymphocytes was measured at 33.8% of the total lymphocytes (equivalent to 557 $CD4^+$ T-lymphocytes in 1650 total lymphocytes).

absolute $CD4^+$ T-lymphocyte count for comparison. Cell counts by conventional hemocytological analysis were: 5300 white blood cells, 2050 total lymphocytes, 600 mixed monocytes, eosinophils, and basophils. Flow cytometry was carried out with a flow cytometer (model Bryte HS, BioRad Laboratories, Inc., Hercules, Calif., USA), equipped with a xenon laser operating at a laser period of 350 to 600 nanometers, and 520 nanometer and 570 nanometer filters (for fluorescein analysis and phycoerythrin analysis, respectively). The flow cytometer was operated with a fluoroscein sensitivity of less than 1000 MESF (molecules of equivalent soluble

TABLE 11

| Streptavidin concentration (micrograms/mL) | | | GRID SECTOR | Cells counted per grid sector | | | | | | | | | Total cells in grid | Absolute $CD4^+$ T-lymphocyte count, cells/μL (discrepancy from FC + H*) | $CD4^+$ T-lymphocytes (% of total lymphocytes) (discrepancy from FC + H*) |
|---|---|---|---|---|---|---|---|---|---|---|---|---|---|---|---|
| | | | | 1 | 2 | 3 | 4 | 5 | 6 | 7 | 8 | 9 | | | |
| 10 | 10 | 10 | $CD4^+$ cells | 19 | 32 | 14 | 24 | 76 | 21 | 21 | 41 | 19 | 267 | 1068 | 64.7% |
| | | | Positive cells | 24 | 31 | 23 | 39 | 87 | 35 | 25 | 56 | 39 | 359 | (511) | (30.9%) |
| 50 | 50 | 50 | $CD4^+$ cells | 2 | 8 | 5 | 16 | 49 | 19 | 9 | 19 | 9 | 136 | 544 | 33.0% |
| | | | Positive cells | 4 | 6 | 5 | 7 | 13 | 8 | 4 | 6 | 4 | 57 | (−13) | (−0.8%) |
| 100 | 100 | 100 | $CD4^+$ cells | 4 | 9 | 5 | 11 | 33 | 10 | 7 | 19 | 8 | 106 | 425 | 25.5% |
| | | | Positive cells | 1 | 2 | 0 | 0 | 6 | 3 | 2 | 4 | 3 | 21 | (−133) | (−8.3%) |

*Values in parentheses give the discrepancy between the absolute $CD4^+$ cell count or percentage, respectively, obtained by the method of the invention (in cells per microliter) from that obtained by flow cytometric $CD4^+$ analysis and hemocytometric cell counts (FC + H).

Anti-CD4 antibody concentration. Cell counts were carried out using whole blood from a healthy volunteer and the procedure described in Example 4, except that the glass slides were treated with solutions of biotinylated anti-human CD4 monoclonal antibody solution at concentrations of 2, 5, or 10 micrograms per milliliter. The sample of diluted whole blood was incubated in the antibody-coated chamber at 18 degrees Celsius and 42% humidity. The results are given in Table 12.

The whole blood sample was also analyzed by flow cytometry and conventional hemocytological analysis to obtain an fluorescein), a scattered light sensitivity of 0.22 micrometers, and a differentiation rate of 0.02 micrometers. A combination CD4/CD8 fluorescent labelling reagent, consisting of fluorescein-labelled anti-human CD4 monoclonal antibody from clone 13B8.2 and phycoerythrin-labelled anti-human CD4 monoclonal antibody from clone B9.11 (Immunotech catalogue number IM 1385, Beckman Coulter, Inc., Fullerton, Calif., USA) was used to label the flow cytometry samples. By flow cytometric analysis, $CD4^+$ T-lymphocytes was measured at 33.3% of the total lymphocytes (equivalent to 682 $CD4^+$ T-lymphocytes in 2050 total lymphocytes).

TABLE 12

| Anti-CD4 antibody concentration (micrograms/mL) | | | GRID SECTOR | Cells counted per grid sector | | | | | | | | | Total cells in grid | Absolute CD4+ T-lymphocyte count, cells/µL (discrepancy from FC + H*) | CD4+ T-lymphocytes (% of total lymphocytes) (discrepancy from FC + H*) |
|---|---|---|---|---|---|---|---|---|---|---|---|---|---|---|---|
| | | | | 1 | 2 | 3 | 4 | 5 | 6 | 7 | 8 | 9 | | | |
| 2 | 2 | 2 | CD4+ cells | 4 | 5 | 3 | 12 | 34 | 9 | 11 | 18 | 8 | 104 | 416 (−266) | 20.3% (−13.0%) |
| | | | Positive cells | 1 | 0 | 2 | 1 | 6 | 2 | 2 | 0 | 0 | 14 | | |
| 5 | 5 | 5 | CD4+ cells | 5 | 18 | 5 | 25 | 43 | 26 | 11 | 27 | 12 | 172 | 688 (6) | 33.6% (0.3%) |
| | | | Positive cells | 2 | 3 | 5 | 2 | 5 | 6 | 2 | 6 | 1 | 32 | | |
| 10 | 10 | 10 | CD4+ cells | 6 | 17 | 4 | 24 | 45 | 19 | 14 | 29 | 15 | 173 | 692 (10) | 33.8% (0.5%) |
| | | | Positive cells | 4 | 12 | 3 | 11 | 20 | 6 | 1 | 11 | 0 | 68 | | |

*Values in parentheses give the discrepancy between the absolute CD4+ cell count or percentage, respectively, obtained by the method of the invention (in cells per microliter) from that obtained by flow cytometric CD4+ analysis and hemocytometric cell counts (FC + H).

Sample incubation time. Cell counts were carried out using whole blood from a healthy volunteer and the procedure described in Example 4. The sample of diluted whole blood was incubated for 10, 20, or 30 minutes in the antibody-coated chamber at 15 degrees Celsius and 46% humidity. The results are given in Table 13.

The whole blood sample was also analyzed by flow cytometry and conventional hemocytological analysis to obtain an absolute CD4+ T-lymphocyte count for comparison. Cell counts by conventional hemocytological analysis were: 5000 white blood cells, 1850 total lymphocytes, 600 mixed monocytes, eosinophils, and basophils. Flow cytometry was carried out with a flow cytometer (model Bryte HS, BioRad Laboratories, Inc., Hercules, Calif., USA), equipped with a xenon laser operating at a laser period of 350 to 600 nanometers, and 520 nanometer and 570 nanometer filters (for fluorescein analysis and phycoerythrin analysis, respectively). The flow cytometer was operated with a fluoroscein sensitivity of less than 1000 MESF (molecules of equivalent soluble fluorescein), a scattered light sensitivity of 0.22 micrometers, and a differentiation rate of 0.02 micrometers. A combination CD4/CD8 fluorescent labelling reagent, consisting of fluorescein-labelled anti-human CD4 monoclonal antibody from clone 13B8.2 and phycoerythrin-labelled anti-human CD4 monoclonal antibody from clone B9.11 (Immunotech catalogue number IM 1385, Beckman Coulter, Inc., Fullerton, Calif., USA) was used to label the flow cytometry samples. By flow cytometric analysis, CD4+ T-lymphocytes was measured at 33.6% of the total lymphocytes (equivalent to 621 CD4+ T-lymphocytes in 1850 total lymphocytes).

TABLE 13

| Sample incubation time (minutes) | | | GRID SECTOR | Cells counted per grid sector | | | | | | | | | Total cells in grid | Absolute CD4+ T-lymphocyte count, cells/µL (discrepancy from FC + H*) | CD4+ T-lymphocytes (% of total lymphocytes) (discrepancy from FC + H*) |
|---|---|---|---|---|---|---|---|---|---|---|---|---|---|---|---|
| | | | | 1 | 2 | 3 | 4 | 5 | 6 | 7 | 8 | 9 | | | |
| 10 | 10 | 10 | CD4+ cells | 3 | 6 | 2 | 17 | 38 | 8 | 15 | 27 | 9 | 125 | 500 (−121) | 27.0% (−6.6%) |
| | | | Positive cells | 0 | 1 | 0 | 2 | 6 | 2 | 5 | 3 | 4 | 23 | | |
| 20 | 20 | 20 | CD4+ cells | 3 | 18 | 3 | 16 | 41 | 24 | 4 | 26 | 11 | 146 | 584 (−37) | 31.6% (−2.0%) |
| | | | Positive cells | 0 | 7 | 2 | 6 | 36 | 8 | 3 | 16 | 9 | 87 | | |
| 30 | 30 | 30 | CD4+ cells | 6 | 7 | 2 | 25 | 35 | 18 | 10 | 17 | 4 | 144 | 576 (−45) | 31.1% (−2.5%) |
| | | | Positive cells | 5 | 16 | 0 | 19 | 29 | 8 | 2 | 15 | 0 | 94 | | |

*Values in parentheses give the discrepancy between the absolute CD4+ cell count or percentage, respectively, obtained by the method of the invention (in cells per microliter) from that obtained by flow cytometric CD4+ analysis and hemocytometric cell counts (FC + H).

Sample incubation temperature. Cell counts were carried out using whole blood from a healthy volunteer and the procedure described in Example 4. The sample of diluted whole blood was incubated in the antibody-coated chamber at 17, 25, or 30 degrees Celsius and 54% humidity. The results are given in Table 14.

Figure 2:
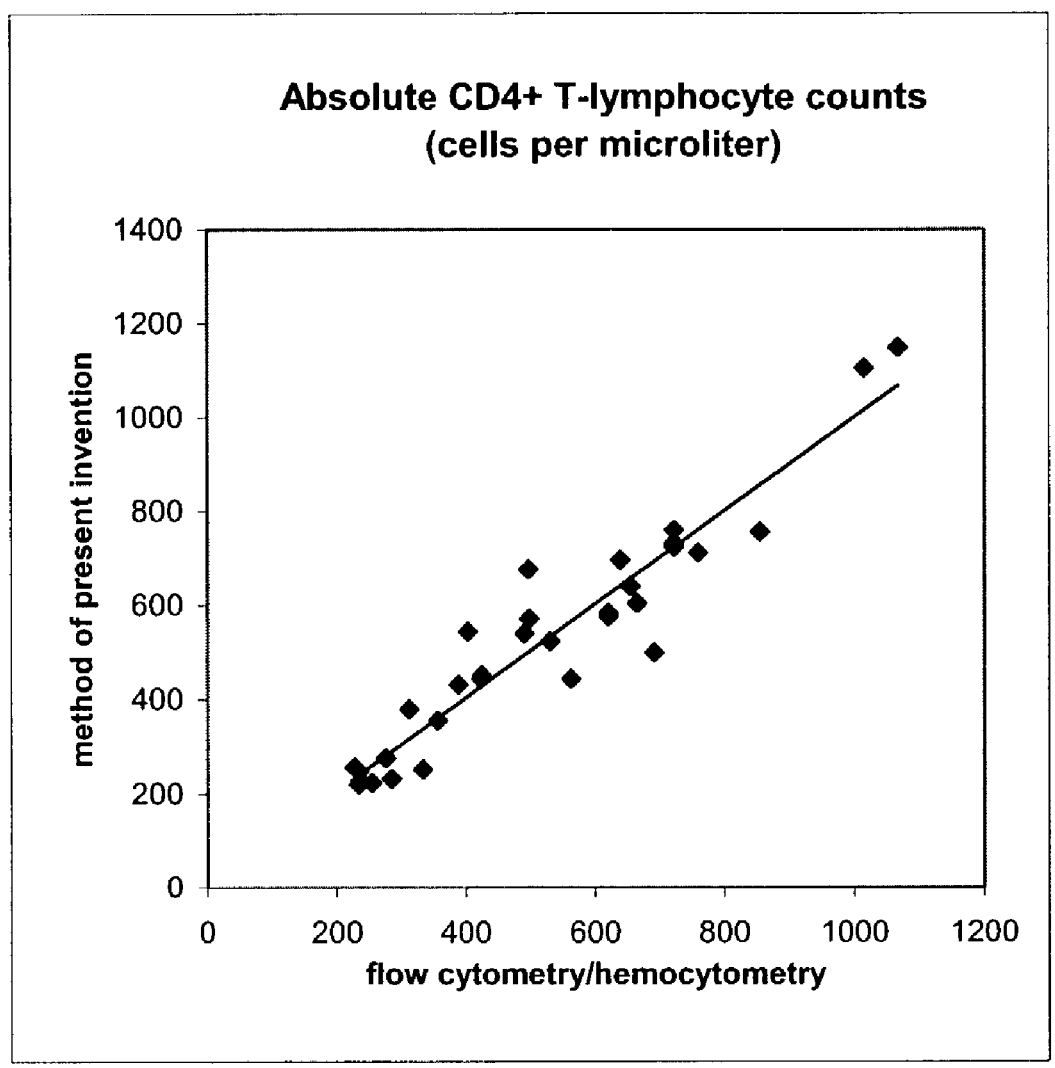
FIG. 2 depicts paired absolute $CD4^+$ T-lymphocyte counts (n=40) in cells per microliter of whole blood, as described in Example 5. The data were obtained by either a method of the present invention such as described in Example 4, or by flow cytometry and hemocytometry.

The whole blood sample was also analyzed by flow cytometry and conventional hemocytological analysis to obtain an absolute $CD4^+$ T-lymphocyte count for comparison. Cell counts by conventional hemocytological analysis were: 5800 white blood cells, 2150 total lymphocytes, 700 mixed monocytes, eosinophils, and basophils. Flow cytometry was carried out with a flow cytometer (model Bryte HS, BioRad Laboratories, Inc., Hercules, Calif., USA), equipped with a xenon laser operating at a laser period of 350 to 600 nanometers, and 520 nanometer and 570 nanometer filters (for fluorescein analysis and phycoerythrin analysis, respectively). The flow cytometer was operated with a fluoroscein sensitivity of less than 1000 MESF (molecules of equivalent soluble fluorescein), a scattered light sensitivity of 0.22 micrometers, and a differentiation rate of 0.02 micrometers. A combination CD4/CD8 fluorescent labelling reagent, consisting of fluorescein-labelled anti-human CD4 monoclonal antibody from clone 13B8.2 and phycoerythrin-labelled anti-human CD4 monoclonal antibody from clone B9.11 (Immunotech catalogue number IM 1385, Beckman Coulter, Inc., Fullerton, Calif., USA) was used to label the flow cytometry samples. By flow cytometric analysis, $CD4^+$ T-lymphocytes was measured at 33.6% of the total lymphocytes (equivalent to 722 $CD4^+$ T-lymphocytes in 2150 total lymphocytes).

from 1 healthy volunteer, 5 samples were from 4 HIV-infected volunteers, and 25 samples were from 24 diseased or otherwise unhealthy volunteers (non-HIV-infected individuals admitted to hospital for treatment of various health conditions). Dilution of the whole blood was 4-fold in all cases. Using the method of the invention as described in Example 4, $CD4^+$ T-lymphocytes were counted. Absolute $CD4^+$ T-lymphocyte counts were calculated by dividing the total $CD4^+$ T-lymphocyte count from nine sectors by the volume in microliters of diluted blood analyzed, and multiplying the result by the dilution factor. Flow cytometric analyses of the same blood samples were also performed using a BioRad Laboratories, Inc. (Hercules, Calif., USA) Bryte HS flow cytometer equipped with a xenon laser operating at a laser period of 350 to 600 nanometers, and 520 nanometer and 570 nanometer filters (for fluorescein analysis and phycoerythrin analysis, respectively). The flow cytometer was operated with a fluoroscein sensitivity of less than 1000 MESF (molecules of equivalent soluble fluorescein), a scattered light sensitivity of 0.22 micrometers, and a differentiation rate of 0.02 micrometers. A combination CD4/CD8 fluorescent labelling reagent, consisting of fluorescein-labelled anti-human CD4 monoclonal antibody from clone 13B8.2 and phycoerythrin-labelled anti-human CD4 monoclonal antibody from clone B9.11 (Immunotech catalogue number IM 1385, Beckman Coulter, Inc., Fullerton, Calif., USA) was used to label the flow cytometry samples. Using flow cytometry, absolute $CD4^+$ T-lymphocyte counts were calculated by multiplying the percentage of $CD4^+$ T-lymphocytes measured by flow cytometry by the absolute lymphocyte count obtained by conventional hemocytological analysis. The results are given in Table 15. Paired absolute $CD4^+$ T-lymphocyte counts obtained from the two methods are given in Table 16 and the same paired data are depicted graphically in FIG. 2. The Pearson correlation coefficient was calculated for the paired data as an measurement of the extent of a linear relationship between the values obtained by the method of the present invention and the values obtained by flow cytometry and hematology; the Pearson correlation coefficient obtained was r=0.947 (p<0.001), and the corresponding coefficient of determination was $r^2$=0.897.

TABLE 14

| Incubation temperature (degrees Celsius) | | | GRID SECTOR | Cells counted per grid sector | | | | | | | | | Total cells in grid | Absolute $CD4^+$ T-lymphocyte count, cells/μL (discrepancy from FC + H*) | $CD4^+$ T-lymphocytes (% of total lymphocytes) (discrepancy from FC + H*) |
|---|---|---|---|---|---|---|---|---|---|---|---|---|---|---|---|
| | | | | 1 | 2 | 3 | 4 | 5 | 6 | 7 | 8 | 9 | | | |
| 17 | 17 | 17 | $CD4^+$ cells | 7 | 2 | 1 | 36 | 48 | 12 | 16 | 36 | 5 | 181 | 724 | 33.7% |
| | | | Positive cells | 4 | 15 | 0 | 22 | 40 | 14 | 7 | 27 | 3 | 132 | (2) | (0.1%) |
| 25 | 25 | 25 | $CD4^+$ cells | 13 | 46 | 6 | 29 | 49 | 22 | 5 | 12 | 1 | 183 | 732 | 34.0% |
| | | | Positive cells | 7 | 33 | 7 | 19 | 62 | 27 | 0 | 9 | 2 | 165 | (10) | (0.4%) |
| 30 | 30 | 30 | $CD4^+$ cells | 19 | 27 | 7 | 43 | 64 | 10 | 3 | 15 | 2 | 190 | 760 | 35.3% |
| | | | Positive cells | 14 | 43 | 4 | 29 | 96 | 9 | 2 | 11 | 1 | 209 | (38) | (1.7%) |

*Values in parentheses give the discrepancy between the absolute $CD4^+$ cell count or percentage, respectively, obtained by the method of the invention (in cells per microliter) from that obtained by flow cytometric $CD4^+$ analysis and hemocytometric cell counts (FC + H).

Example 5

Comparison of Cell Counts Obtained by Different Methods

The following example describes the determination of absolute cell counts obtained by a method of the present invention and by flow cytometry and hemocytometry. Unless otherwise specified, all reagent sources were the same as those in Example 1.

Samples of whole blood were obtained by aseptic venipuncture from 32 volunteers as follows: 10 samples were

TABLE 15

| Date | Sample Number (Subject ID) | Target cell binding conditions | FC + H results | Grid Sector | Cells counted per grid sector | | | | | | | | | Total cells in grid | Absolute CD4+ T-lymphocyte count, cells/μL (discrepancy from FC + H*) | CD4+ T-lymphocytes (% of total lymphocytes) (discrepancy from FC + H*) |
|---|---|---|---|---|---|---|---|---|---|---|---|---|---|---|---|---|
| | | | | | 1 | 2 | 3 | 4 | 5 | 6 | 7 | 8 | 9 | | | |
| 7 Feb. 2003 | 1 (TC) healthy | 15 degrees C. 46% humidity | WBC: 5000 LYM: 1850 CD4+: 621 (33.6%) | CD4+ cells | 3 | 18 | 3 | 16 | 41 | 24 | 4 | 26 | 11 | 146 | 584 (−37) | 31.6% (−2.0%) |
| | | | | Positive cells | 0 | 7 | 2 | 6 | 36 | 8 | 3 | 16 | 9 | 87 | | |
| 7 Feb. 2003 | 2 (TC) healthy | 15 degrees C. 46% humidity | WBC: 5000 LYM: 1850 CD4+: 621 (33.6%) | CD4+ cells | 6 | 7 | 2 | 25 | 35 | 18 | 10 | 17 | 4 | 144 | 576 (−45) | 31.1% (−2.5%) |
| | | | | Positive cells | 5 | 16 | 0 | 19 | 29 | 8 | 2 | 15 | 1 | 94 | | |
| 10 Feb. 2003 | 3 (TC) healthy | 17 degrees C. 54% humidity | WBC: 5800 LYM: 2150 CD4+: 722 (33.6%) | CD4+ cells | 7 | 20 | 1 | 36 | 48 | 12 | 16 | 36 | 5 | 181 | 724 (2) | 33.7% (0.1%) |
| | | | | Positive cells | 4 | 15 | 0 | 22 | 40 | 14 | 7 | 27 | 3 | 132 | | |
| 10 Feb. 2003 | 4 (TC) healthy | 17 degrees C. 54% humidity | WBC: 5800 LYM: 2150 CD4+: 722 (33.6%) | CD4+ cells | 13 | 46 | 6 | 29 | 49 | 22 | 5 | 12 | 1 | 183 | 732 (10) | 34.0% (0.4%) |
| | | | | Positive cells | 7 | 33 | 7 | 19 | 62 | 27 | 0 | 9 | 2 | 165 | | |
| 10 Feb. 2003 | 5 (TC) healthy | 17 degrees C. 54% humidity | WBC: 5800 LYM: 2150 CD4+: 722 (33.6%) | CD4+ cells | 19 | 27 | 7 | 43 | 64 | 10 | 3 | 15 | 2 | 190 | 760 (38) | 35.3% (1.7%) |
| | | | | Positive cells | 14 | 43 | 4 | 29 | 96 | 9 | 2 | 11 | 1 | 209 | | |
| 12 Feb. 2003 | 6 (TC) healthy | 15 degrees C. 36% humidity | WBC: 5400 LYM: 1950 CD4+: 655 (33.6%) | CD4+ cells | 3 | 12 | 1 | 28 | 39 | 26 | 16 | 26 | 9 | 160 | 640 (−15) | 32.8% (−0.8%) |
| | | | | Positive cells | 1 | 4 | 0 | 9 | 7 | 7 | 4 | 13 | 5 | 50 | | |
| 12 Feb. 2003 | 7 (A) diseased | 15 degrees C. 36% humidity | WBC: 5700 LYM: 1308 CD4+: 425 (32.5%) | CD4+ cells | 0 | 9 | 2 | 16 | 45 | 16 | 4 | 18 | 3 | 113 | 452 (27) | 34.6% (2.1%) |
| | | | | Positive cells | 1 | 8 | 0 | 15 | 25 | 8 | 1 | 16 | 2 | 76 | | |
| 12 Feb. 2003 | 8 (B) diseased | 15 degrees C. 36% humidity | WBC: 6600 LYM: 2200 CD4+: 1016 (46.2%) | CD4+ cells | 5 | 18 | 1 | 49 | 72 | 29 | 23 | 64 | 15 | 276 | 1104 (88) | 50.2% (4.0%) |
| | | | | Positive cells | 0 | 10 | 0 | 11 | 27 | 7 | 8 | 22 | 1 | 84 | | |
| 14 Feb. 2003 | 9 (C) diseased | 16 degrees C. 52% humidity | WBC: 7200 LYM: 957 CD4+: 255 (26.7%) | CD4+ cells | 4 | 1 | 1 | 17 | 20 | 4 | 2 | 6 | 1 | 56 | 224 (−31) | 23.4% (−3.3%) |
| | | | | Positive cells | 2 | 8 | 0 | 24 | 68 | 12 | 8 | 8 | 9 | 109 | | |
| 14 Feb. 2003 | 10 (D) diseased | 16 degrees C. 52% humidity | WBC: 5900 LYM: 1807 CD4+: 285 (15.8%) | CD4+ cells | 1 | 7 | 3 | 11 | 13 | 4 | 4 | 9 | 6 | 58 | 232 (−53) | 12.8% (−3.0%) |
| | | | | Positive cells | 1 | 3 | 1 | 4 | 4 | 0 | 0 | 6 | 1 | 20 | | |
| 14 Feb. 2003 | 11 (E) diseased | 16 degrees C. 52% humidity | WBC: 5000 LYM: 1155 CD4+: 356 (30.8%) | CD4+ cells | 4 | 6 | 5 | 12 | 32 | 13 | 4 | 11 | 2 | 89 | 356 (0) | 30.8% (0%) |
| | | | | Positive cells | 1 | 9 | 0 | 15 | 23 | 4 | 2 | 6 | 4 | 64 | | |
| 14 Feb. 2003 | 12 (F) diseased | 16 degrees C. 52% humidity | WBC: 7450 LYM: 3113 CD4+: 759 (24.4%) | CD4+ cells | 8 | 25 | 2 | 30 | 48 | 15 | 9 | 38 | 3 | 178 | 712 (−47) | 22.9% (−1.5%) |
| | | | | Positive cells | 0 | 1 | 0 | 2 | 3 | 0 | 0 | 5 | 0 | 11 | | |
| 14 Feb. 2003 | 13 (G) diseased | 16 degrees C. 52% humidity | WBC: 4700 LYM: 1800 CD4+: 691 (38.4%) | CD4+ cells | 5 | 30 | 5 | 10 | 38 | 17 | 4 | 14 | 2 | 125 | 500 (−191) | 27.7% (−10.7%) |
| | | | | Positive cells | 4 | 15 | 1 | 5 | 4 | 7 | 4 | 6 | 2 | 48 | | |
| 17 Feb. 2003 | 14 (H) diseased | 16 degrees C. 58% humidity | WBC: 6500 LYM: 1748 CD4+: 403 (23.1%) | CD4+ cells | 0 | 0 | 1 | 24 | 46 | 22 | 12 | 21 | 10 | 136 | 544 (141) | 31.1% (8.0%) |
| | | | | Positive cells | 1 | 3 | 0 | 20 | 46 | 15 | 8 | 26 | 12 | 134 | | |
| 17 Feb. 2003 | 15 (I) diseased | 16 degrees C. 58% humidity | WBC: 5700 LYM: 1812 CD4+: 639 (35.3%) | CD4+ cells | 3 | 12 | 2 | 19 | 71 | 22 | 5 | 31 | 9 | 174 | 696 (57) | 38.4% (3.1%) |
| | | | | Positive cells | 0 | 5 | 2 | 7 | 12 | 2 | 1 | 10 | 5 | 44 | | |
| 17 Feb. 2003 | 16 (J) diseased | 16 degrees C. 58% humidity | WBC: 4800 LYM: 1344 CD4+: 228 (17.0%) | CD4+ cells | 0 | 8 | 1 | 5 | 25 | 5 | 1 | 15 | 4 | 64 | 256 (28) | 19.0% (2.0%) |
| | | | | Positive cells | 1 | 3 | 1 | 7 | 18 | 8 | 1 | 13 | 4 | 56 | | |
| 17 Feb. 2003 | 17 (K) diseased | 16 degrees C. 58% humidity | WBC: 9600 LYM: 2812 CD4+: 1068 (38.0%) | CD4+ cells | 9 | 9 | 12 | 41 | 102 | 23 | 23 | 56 | 12 | 287 | 1148 (80) | 40.8% (2.8%) |
| | | | | Positive cells | 0 | 1 | 0 | 3 | 6 | 2 | 4 | 4 | 1 | 21 | | |

TABLE 15-continued

| Date | Sample Number (Subject ID) | Target cell binding conditions | FC + H results | Grid Sector | \multicolumn{9}{c}{Cells counted per grid sector} | Total cells in grid | Absolute CD4+ T-lymphocyte count, cells/µL (discrepancy from FC + H*) | CD4+ T-lymphocytes (% of total lymphocytes) (discrepancy from FC + H*) |
|---|---|---|---|---|---|---|---|---|---|---|---|---|---|---|---|---|
| | | | | | 1 | 2 | 3 | 4 | 5 | 6 | 7 | 8 | 9 | | | |
| 18 Feb. 2003 | 18 (TC) healthy | 16 degrees C. 54% humidity | WBC: 4900 LYM: 1440 CD4+: 491 (34.1%) | CD4+ cells | 3 | 11 | 2 | 18 | 56 | 13 | 4 | 24 | 4 | 135 | 540 (49) | 37.5% (2.4%) |
| | | | | Positive cells | 4 | 4 | 2 | 7 | 13 | 8 | 8 | 8 | 1 | 55 | | |
| 20 Feb. 2003 | 19 (L) diseased | 18 degrees C. 36% humidity | WBC: 5800 LYM: 1800 CD4+: 531 (29.5%) | CD4+ cells | 9 | 2 | 2 | 17 | 41 | 7 | 8 | 25 | 2 | 131 | 524 (−7) | 29.1% (−0.4%) |
| | | | | Positive cells | 2 | 8 | 1 | 8 | 19 | 1 | 4 | 12 | 0 | 55 | | |
| 21 Feb. 2003 | 20 (M) diseased | 19 degrees C. 48% humidity | WBC: 6000 LYM: 1900 CD4+: 467 (26.2%) | CD4+ cells | 7 | 13 | 6 | 19 | 51 | 21 | 18 | 31 | 3 | 169 | 676 (179) | 35.6% (9.4%) |
| | | | | Positive cells | 3 | 10 | 2 | 7 | 13 | 3 | 4 | 9 | 2 | 54 | | |
| 21 Feb. 2003 | 21 (N) diseased | 19 degrees C. 48% humidity | WBC: 6200 LYM: 2700 CD4+: 855 (31.7%) | CD4+ cells | 8 | 40 | 7 | 28 | 50 | 30 | 5 | 15 | 6 | 189 | 756 (−99) | 28.0% (−3.7%) |
| | | | | Positive cells | 4 | 8 | 4 | 13 | 36 | 7 | 3 | 8 | 3 | 86 | | |
| 21 Feb. 2003 | 22 (O) diseased | 19 degrees C. 48% humidity | WBC: 6100 LYM: 2153 CD4+: 665 (30.9%) | CD4+ cells | 1 | 18 | 10 | 1 | 57 | 35 | 0 | 21 | 8 | 151 | 604 (−61) | 28.1% (−2.8%) |
| | | | | Positive cells | 1 | 16 | 2 | 9 | 51 | 14 | 0 | 11 | 4 | 108 | | |
| 21 Feb. 2003 | 23 (P) diseased | 19 degrees C. 48% humidity | WBC: 3700 LYM: 1480 CD4+: 563 (38.1%) | CD4+ cells | 4 | 20 | 7 | 7 | 38 | 16 | 1 | 12 | 6 | 111 | 444 (−119) | 30.0% (−8.1%) |
| | | | | Positive cells | 2 | 8 | 6 | 9 | 31 | 11 | 2 | 9 | 4 | 82 | | |
| 21 Feb. 2003 | 24 (Q) diseased | 19 degrees C. 48% humidity | WBC: 4600 LYM: 800 CD4+: 276 (34.6%) | CD4+ cells | 0 | 10 | 1 | 6 | 30 | 10 | 1 | 11 | 0 | 69 | 276 (0) | 34.5% (0%) |
| | | | | Positive cells | 1 | 9 | 0 | 6 | 24 | 6 | 1 | 7 | 3 | 57 | | |
| 25 Feb. 2003 | 25 (R) diseased | 18 degrees C. 44% humidity | WBC: 8200 LYM: 844 CD4+: 424 (50.3%) | CD4+ cells | 0 | 9 | 0 | 26 | 39 | 13 | 5 | 18 | 1 | 111 | 444 (20) | 52.6% (2.3%) |
| | | | | Positive cells | 0 | 2 | 0 | 11 | 24 | 6 | 2 | 6 | 0 | 51 | | |
| 25 Feb. 2003 | 26 (S) diseased | 18 degrees C. 44% humidity | WBC: 10500 LYM: 2866 CD4+: 498 (17.4%) | CD4+ cells | 3 | 10 | 2 | 17 | 58 | 21 | 3 | 21 | 8 | 143 | 572 (74) | 20.0% (2.6%) |
| | | | | Positive cells | 1 | 10 | 2 | 8 | 41 | 13 | 2 | 10 | 3 | 90 | | |
| 25 Feb. 2003 | 27 (T) diseased | 18 degrees C. 44% humidity | WBC: 3600 LYM: 1018 CD4+: 312 (30.7%) | CD4+ cells | 4 | 10 | 0 | 15 | 45 | 6 | 3 | 11 | 1 | 95 | 380 (68) | 37.3% (6.6%) |
| | | | | Positive cells | 1 | 8 | 1 | 15 | 31 | 2 | 4 | 5 | 0 | 67 | | |
| 27 Feb. 2003 | 28 (HIV-1) HIV-infected | 17 degrees C. 55% humidity | WBC: 4800 LYM: 1688 CD4+: 236 (14.0%) | CD4+ cells | 3 | 10 | 1 | 9 | 18 | 5 | 5 | 6 | 2 | 57 | 228 (−8) | 13.5% (−0.5%) |
| | | | | Positive cells | 0 | 11 | 0 | 12 | 38 | 14 | 1 | 7 | 0 | 83 | | |
| 27 Feb. 2003 | 29 (HIV-2) HIV-infected | 17 degrees C. 55% humidity | WBC: 5300 LYM: 2700 CD4+: 388 (14.4%) | CD4+ cells | 5 | 6 | 1 | 22 | 44 | 5 | 5 | 14 | 6 | 108 | 432 (44) | 16.0% (1.6%) |
| | | | | Positive cells | 1 | 3 | 2 | 6 | 20 | 7 | 1 | 5 | 1 | 46 | | |
| 27 Feb. 2003 | 30 (HIV-3) HIV-infected | 17 degrees C. 55% humidity | WBC: 4650 LYM: 2164 CD4+: 333 (15.4%) | CD4+ cells | 1 | 4 | 1 | 6 | 30 | 6 | 5 | 7 | 3 | 63 | 252 (−81) | 11.6% (−3.8%) |
| | | | | Positive cells | 1 | 4 | 0 | 8 | 17 | 6 | 2 | 13 | 1 | 52 | | |
| 27 Feb. 2003 | 31 (HIV-4) HIV-infected | 17 degrees C. 55% humidity | WBC: 3400 LYM: 1065 CD4+: 234 (22.0%) | CD4+ cells | 1 | 9 | 0 | 9 | 24 | 5 | 4 | 10 | 0 | 62 | 248 (14) | 23.3% (1.3%) |
| | | | | Positive cells | 0 | 3 | 0 | 13 | 24 | 3 | 3 | 15 | 1 | 62 | | |
| 27 Feb. 2003 | 32 (HIV-4) HIV-infected | 17 degrees C. 55% humidity | WBC: 3400 LYM: 1065 CD4+: 234 (22.0%) | CD4+ cells | 1 | 1 | 1 | 8 | 18 | 8 | 4 | 13 | 1 | 55 | 220 (−14) | 20.7% (−1.3%) |
| | | | | Positive cells | 0 | 2 | 0 | 7 | 21 | 10 | 4 | 17 | 1 | 62 | | |
| 12 Mar. 2003 | 33 (TC) healthy | 17 degrees C. 52% humidity | WBC: 5700 LYM: 1877 CD4+: 619 (33.0%) | CD4+ cells | 3 | 11 | 4 | 21 | 57 | 20 | 5 | 27 | 6 | 154 | 614 (−5) | 32.6% (−0.4%) |
| | | | | Positive cells | 0 | 1 | 1 | 14 | 24 | 7 | 5 | 12 | 1 | 64 | | |
| 18 Mar. 2003 | 34 (TC) healthy | 17 degrees C. 55% humidity | WBC: 6400 LYM: 2000 CD4+: 640 (32.0%) | CD4+ cells | 14 | 18 | 6 | 18 | 51 | 15 | 6 | 13 | 5 | 146 | 584 (−56) | 29.2% (−2.8%) |
| | | | | Positive cells | 4 | 11 | 1 | 8 | 21 | 6 | 0 | 10 | 0 | 61 | | |

TABLE 15-continued

| Date | Sample Number (Subject ID) | Target cell binding conditions | FC + H results | Grid Sector | Cells counted per grid sector | | | | | | | | | Total cells in grid | Absolute CD4+ T-lymphocyte count, cells/μL (discrepancy from FC + H*) | CD4+ T-lymphocytes (% of total lymphocytes) (discrepancy from FC + H*) |
|---|---|---|---|---|---|---|---|---|---|---|---|---|---|---|---|---|
| | | | | | 1 | 2 | 3 | 4 | 5 | 6 | 7 | 8 | 9 | | | |
| 18 Mar. 2003 | 35 (TC) healthy | 17 degrees C. 55% humidity | WBC: 6400 LYM: 2000 CD4+: 640 (32.0%) | CD4+ cells Positive cells | 3 2 | 9 12 | 3 2 | 24 15 | 44 39 | 26 15 | 7 1 | 35 10 | 5 4 | 156 100 | 624 (−16) | 31.2% (−0.8%) |
| 18 Mar. 2003 | 36 (U) diseased | 17 degrees C. 55% humidity | WBC: 4500 LYM: 1400 CD4+: 483 (34.5%) | CD4+ cells Positive cells | 4 2 | 18 5 | 4 0 | 8 7 | 29 8 | 8 1 | 2 4 | 19 4 | 5 0 | 97 31 | 388 (−95) | 27.7% (−6.8%) |
| 18 Mar. 2003 | 37 (U) diseased | 17 degrees C. 55% humidity | WBC: 4500 LYM: 1400 CD4+: 483 (34.5%) | CD4+ cells Positive cells | 4 2 | 10 4 | 3 0 | 21 2 | 26 21 | 9 6 | 6 0 | 15 6 | 1 1 | 95 42 | 380 (−103) | 27.1% (−7.4%) |
| 20 Mar. 2003 | 38 (V) diseased | 18 degrees C. 48% humidity | WBC: 5900 LYM: 2700 CD4+: 669 (24.8%) | CD4+ cells Positive cells | 3 2 | 18 8 | 2 0 | 24 13 | 54 33 | 16 11 | 13 5 | 25 6 | 4 8 | 159 86 | 636 (−33) | 23.6% (−1.2%) |
| 20 Mar. 2003 | 39 (W) diseased | 18 degrees C. 48% humidity | WBC: 6900 LYM: 1200 CD4+: 318 (26.5%) | CD4+ cells Positive cells | 1 2 | 7 7 | 0 2 | 15 14 | 24 24 | 7 10 | 6 0 | 19 15 | 1 0 | 80 74 | 320 (2) | 26.7% (0.2%) |
| 20 Mar. 2003 | 40 (X) diseased | 18 degrees C. 48% humidity | WBC: 6500 LYM: 2000 CD4+: 588 (29.4%) | CD4+ cells Positive cells | 15 3 | 13 5 | 4 3 | 24 13 | 44 30 | 20 8 | 8 6 | 22 9 | 4 4 | 154 81 | 616 (28) | 30.8% (1.4%) |

*Values in parentheses give the discrepancy between the absolute CD4+ cell count or percentage, respectively, obtained by the method of the invention (in cells per microliter) from that obtained by flow cytometric CD4+ analysis and hemocytometric cell counts (FC + H)

TABLE 16

| Sample Number (n = 40) | Subject ID | Health State of Subject | Absolute CD4+ T-lymphocyte counts (cells per microliter) | |
|---|---|---|---|---|
| | | | Flow cytometry and hemocytometry | Method of the present invention |
| 1 | TC | healthy | 621 | 584 |
| 2 | TC | healthy | 621 | 576 |
| 3 | TC | healthy | 722 | 724 |
| 4 | TC | healthy | 722 | 732 |
| 5 | TC | healthy | 722 | 760 |
| 6 | TC | healthy | 655 | 640 |
| 7 | A | diseased | 425 | 452 |
| 8 | B | diseased | 1016 | 1104 |
| 9 | C | diseased | 255 | 224 |
| 10 | D | diseased | 285 | 232 |
| 11 | E | diseased | 356 | 356 |
| 12 | F | diseased | 759 | 712 |
| 13 | G | diseased | 691 | 500 |
| 14 | H | diseased | 403 | 544 |
| 15 | I | diseased | 639 | 696 |
| 16 | J | diseased | 228 | 256 |
| 17 | K | diseased | 1068 | 1148 |
| 18 | TC | healthy | 491 | 540 |
| 19 | L | diseased | 531 | 524 |
| 20 | M | diseased | 497 | 676 |
| 21 | N | diseased | 855 | 756 |
| 22 | O | diseased | 665 | 604 |
| 23 | P | diseased | 563 | 444 |
| 24 | Q | diseased | 276 | 276 |
| 25 | R | diseased | 424 | 444 |
| 26 | S | diseased | 498 | 572 |
| 27 | T | diseased | 312 | 380 |
| 28 | HIV-1 | HIV infected | 236 | 228 |
| 29 | HIV-2 | HIV infected | 388 | 432 |
| 30 | HIV-3 | HIV infected | 333 | 252 |
| 31 | HIV-4 | HIV infected | 234 | 248 |
| 32 | HIV-4 | HIV infected | 234 | 220 |
| 33 | TC | healthy | 619 | 614 |
| 34 | TC | healthy | 640 | 584 |
| 35 | TC | healthy | 640 | 624 |
| 36 | U | diseased | 483 | 388 |
| 37 | U | diseased | 483 | 380 |
| 38 | V | diseased | 669 | 636 |
| 39 | W | diseased | 318 | 320 |
| 40 | X | diseased | 588 | 616 |

All publications, including patent documents and scientific articles, referred to in this application and the bibliography and attachments are incorporated by reference in their entirety for all purposes to the same extent as if each individual publication were individually incorporated by reference.

All headings are for the convenience of the reader and should not be used to limit the meaning of the text that follows the heading, unless so specified.

What is claimed is:

1. A method for observing a target cell in a sample of untreated or substantially untreated whole blood, comprising:
   a) providing a sample of untreated or substantially untreated whole blood that is suspected of containing a target cell;

b) providing a solid substrate, said solid substrate comprising:
a multi-layered composition comprising:
(i) a first component on the surface of said solid substrate, said first component comprises polyanion layers and polycation layers in an alternating arrangement substantially parallel to the surface of said solid substrate;
(ii) a second component contacting said first component, said second component comprises a high affinity binding pair comprising a first member and a second member, wherein the first member binds to said first component, the second member binds to said first member; and
(iii) a third component comprising a specific binding agent that binds to said second member of said second component;
c) contacting said sample with said solid substrate;
d) incubating said sample on said solid substrate for a period of time sufficient to permit said binding agent to specifically bind said target cells present in said sample to said solid substrate;
e) washing said solid substrate; and
f) manually observing and counting the number of said target cells bound to said solid substrate by light microscopy.

2. The method of claim 1, wherein accuracy of said method correlates with quantification by flow cytometry.

3. The method of claim 1, wherein said observation of said target cells bound to said solid substrate correlates with diagnosis of a health condition.

4. The method of claim 3, wherein said health condition is selected from the group consisting of acquired immune deficiency disorders, congenital immune deficiency disorders, leukemias, non-leukemia cancers, idiopathic lymphocytopenias, bacterial infections, parasitic infections, and viral infections.

5. The method of claim 1, wherein said observation of said target cells bound to said solid substrate correlates with prognosis of a health condition.

6. The method of claim 5, wherein said health condition is selected from the group consisting of acquired immune deficiency disorders, congenital immune deficiency disorders, leukemias, non-leukemia cancers, idiopathic lymphocytopenias, bacterial infections, parasitic infections, and viral infections.

7. The method of claim 1, wherein said observation of said target cells bound to said solid substrate correlates with monitoring of a health condition.

8. The method of claim 7, wherein said health condition is selected from the group consisting of acquired immune deficiency disorders, congenital immune deficiency disorders, leukemias, non-leukemia cancers, idiopathic lymphocytopenias, bacterial infections, parasitic infections, and viral infections.

9. The method of claim 1, wherein said target cell is selected from the group consisting of erythrocytes, lymphocytes, monocytes, megakaryocytes, granulocytes, hematopoietic stem cells, hematopoietic progenitor cells, dendritic cells, Langerhans cells, epithelial cells, fibroblasts, metastatic cancer cells, and circulating fetal cells.

10. The method of claim 1, wherein said target cell is selected from the group consisting of a $CD4^+$ T-lymphocyte, a $CD8^+$ T-lymphocyte, a $CD3^+$ T-lymphocyte, a $CD19^+$ B-lymphocyte, a $CD23^+$ B-lymphocyte, a $CD25^+$ T-lymphocyte, a $CD56^+$ natural killer lymphocyte, a $CD65^+$ lymphocyte, and a $CD34^+$ hematopoietic progenitor cell.

11. The method of claim 1, wherein said sample of untreated or substantially untreated whole blood has not been treated for erythrocyte lysis.

12. The method of claim 1, wherein said sample of untreated or substantially untreated whole blood has not been subjected to cell concentration, centrifugation, filtration, buffy coat preparation, plasma removal, serum removal, or isolation of a group of cells.

13. The method of claim 1, wherein said solid substrate is substantially optically transparent.

14. The method of claim 1, wherein said solid substrate is selected from the group consisting of glass, quartz, silicon, silica oxides, ceramics, polymeric plastics, cycloolefins, cellulose polymers, metals, and composites thereof.

15. The method of claim 1, wherein said solid substrate comprises a glass slide.

16. The method of claim 1, wherein said solid substrate comprises a substantially planar surface.

17. The method of claim 1, wherein said solid substrate comprises a chamber.

18. The method of claim 17, wherein said chamber is of predetermined dimensions.

19. The method of claim 18, wherein said chamber comprises a pattern of predetermined dimensions.

20. The method of claim 1, wherein a pattern of predetermined dimensions aids in said observation of said target cells bound to said solid substrate.

21. The method of claim 1, wherein said sample that contacts said solid substrate is of a predetermined volume.

22. The method of claim 1, wherein the polyanions are selected from the group consisting of polyphosphorus acids, polysulphur acids, polyboric acids, polysilicic acids, polycarboxylic acids, anionic polyaminoacids, anionic polypeptides, anionic polyols, anionic polythiols, anionic polyimides, and combinations thereof.

23. The method of claim 1, wherein the polycations are selected from the group consisting of polyamines, polyaminiums, polyammoniums, polyphosphoniums, polyyliums, polyoxoniums, cationic polyols, cationic polythiols, cationic polyaminoacids, cationic polyaldehydes, and combinations thereof.

24. The method of claim 1, wherein said binding agent is selected from the group consisting of antibodies, antibody fragments, antigen-binding sites of antibodies, antigens, ligands, and receptors.

25. The method of claim 1, where said high affinity binding pair is selected from the group consisting of avidin and biotin, protein A and immunoglobulin, protein G and immunoglobulin, protein L and immunoglobulin, and a ligand-receptor pair.

26. The method of claim 1, wherein the top polyionic layer of said first component of said multi-layered composition is covalently bound to said first member of said high affinity binding pair of said second component.

27. The method of claim 1, wherein said period of time is a period of between about 5 and about 300 minutes.

28. The method of claim 1, wherein said period of time is a period of between about 10 and about 120 minutes.

29. The method of claim 1, wherein said period of time is a period of between about 10 and about 60 minutes.

30. The method of claim 1, wherein incubation is carried out at a temperature of between about 4 degrees Celsius and about 40 degrees Celsius.

31. The method of claim 1, wherein incubation is carried out at a temperature of between about 10 degrees Celsius and about 37 degrees Celsius.

32. The method of claim 1, wherein incubation is carried out at a temperature of between about 15 degrees Celsius and about 30 degrees Celsius.

33. The method of claim 1, wherein said observation of said target cells bound to said solid substrate is by optical methods.

34. The method of claim 1, further comprising staining or dyeing said target cells bound to solid substrate to distinguish a subset of cells among said target cells.

35. The method of claim 1, wherein said counting of said target cells bound to said solid substrate may be used to calculate the absolute number of said target cells in a given volume of said sample.

36. The method of claim 1, wherein said first member of a high affinity binding pair of said second component is biotin, said second member of a high affinity binding pair of said second component is avidin, said specific binding agent of said third component is biotinylated, said first member and said specific binding agent bind to said second member through biotin-avidin interaction.

37. The method of claim 1, wherein said second member of a high affinity binding pair of said second component is multivalent and can bind to more than one units of said first member.

38. The method of claim 37, wherein said second member binds to two units of said first member so that said second member forms a layer between two layers of said first member, said specific binding agent is attached to the solid substrate through binding of said second member to said two units of said first member.

39. The method of claim 1, wherein the polyanions are selected from the group consisting of anionic polyimides, anionic polyaminoacids, polysilicic acids, and combinations thereof.

40. The method of claim 39, wherein the polyanions are anionic polyimides.

41. The method of claim 1, wherein the polycations are selected from the group consisting of cationic polyaminoacids, polyamines, polyphosphoniums, and combinations thereof.

42. The method of claim 41, wherein the polycations are polyaminoacids.

43. The method of claim 1, wherein the polyanions and polycations are anionic polyimides and polyaminoacids.

44. The method of claim 1, further comprising staining or dyeing said target cells to enhance observation of said target cells.

* * * * *